United States Patent [19]
Hansen

[11] Patent Number: 5,885,811
[45] Date of Patent: Mar. 23, 1999

[54] LEADER SEQUENCE INDUCING A POST-TRANSLATIONAL MODIFICATION OF POLYPEPTIDES IN BACTERIA GENE THEREFOR AND SUBTILIN VARIANT OF ENHANCED STABILITY AND ACTIVITY

[75] Inventor: J. Norman Hansen, Silver Spring, Md.

[73] Assignee: University of Maryland, College Park, Md.

[21] Appl. No.: 465,491

[22] Filed: Jun. 5, 1995

Related U.S. Application Data

[60] Continuation of Ser. No. 220,033, Mar. 30, 1994, Pat. No. 5,576,420, which is a division of Ser. No. 981,525, Nov. 25, 1992, Pat. No. 5,516,682, which is a continuation-in-part of Ser. No. 214,959, Jul. 5, 1988, Pat. No. 5,218,101.

[51] Int. Cl.$^6$ .............................. C12N 15/11; C12P 21/02; C07H 21/04; C07K 19/32
[52] U.S. Cl. .................. 435/172.3; 435/69.1; 435/252.3; 435/320.1; 530/300; 530/324; 536/23.1
[58] Field of Search ................................ 435/69.1, 172.3, 435/252.3, 320.1; 530/300, 324; 536/23.1

[56] References Cited

U.S. PATENT DOCUMENTS

| | | | |
|---|---|---|---|
| 5,218,101 | 6/1993 | Hansen | 536/23.7 |
| 5,516,682 | 5/1996 | Hansen | 435/252.3 |
| 5,576,420 | 11/1996 | Hansen | 435/69.1 |

FOREIGN PATENT DOCUMENTS

WO 90/00558  1/1990  WIPO .
WO 92/18633  10/1992  WIPO .

OTHER PUBLICATIONS

Wei Lui & J. Norman Hanse, "Enhancement of the Chemical and Antimicrobial properties of Subtiline by Site–directed Mutagenesis", The Journal of Biological Chemistry, (1992) The American Society for Biochemistry and Molecular Biology, Inc., vol., 267, No. 35, Dec. 15, 1992, pp. 25078–25085.

*Primary Examiner*—Nancy Degen
*Attorney, Agent, or Firm*—Oblon, Spivak, McClelland, Maier & Neustadt, P.C.

[57] ABSTRACT

The method by which polypeptides having residues other than the 20 common amino acids are made is established. A leader peptide sequence (SEQ ID NO: 7) and its gene are identified which induce or assist post-translational modifications of Cys, Thr and Ser in prokaryotes. The leader sequence may be used to induce the presence of covalent bonding sites in polypeptides and can be expressed by either naturally occurring or artificial means. Further, a subtilin mutant substituting isoleucine for $Glu_4$ of the native sequence exhibits a 57-fold improvement in stability, resisting modification of the dehydroalanine residue at position 5. This stable mutant exhibits 3–4 times the specific activity, in suppression of bacterial spore outgrowth, of the native bacteriocin. A method for site-specific mutagenesis, as well as the resulting mutant gene, plasmid and transformant is similarly set forth.

16 Claims, 13 Drawing Sheets

```
                                                              12                         24                         36                            a gat ca          60
                                                                                                                                                    (-35)
CCG GAC AGG AGT ATT TTA AGG AAG AGC TTC AAG AGT TAA ACA AAA GAT CAT GAG CTA CTA
                       tta tat    g att cca       (mRNA)                                                                                                            120
                        (-10)     (+1)
TGA CAA GGA TTA TAT CTT TGG ATT CCA TAA CTA TGA ATC AAT GGA AGG GGA CGA AGC AGT
                                                 144                                                             168                                                180
ACC TTT GCA GTA CGT TGG TTT GTT GGA TGG AGC TGT AGG TGT AGG CTT AGG GGT ATT AAA
                 192                                  204                                        216                                                                240
CAT GGA ATT AGG CTC AAA AAC AGA TTG GAC AAA AGC ATT ATT AAT TTA ATA AAA AAA GGA
           252                                  264                                 276                                       (r.b.s.)
AAA AAA TGA TAA AAT CTT TGT CTG TTA CTA TTT AGG TAT TGA AAG GAG GTG ACC
                                                                                                                              sss sss s
################# ---   --- TC-  ---   ---  -T  --G  ---  --G  --C  ---  --C  --G  --A  --C  --T
AAT ATG TCA AAG TTC GAT GAT TTC GAT GTT GTG AAA GTC TCT AAA CAA GAC TCA
MET Ser Lys Phe Asp Asp Phe Asp Val Val Lys Val Ser Lys Gln Asp Ser
                            (leader region)
####################  ---   ---  TC-  ---   ---  -T-  -G-  -C-  ---  --G  --C  ---  --C  --A  --C  --T
AAA ATC ACT CCG CAA TGG AAA AGT GAA TCA CTT TGT ACA GGA TGT GTA ACT GGT GCA
Lys Ile Thr Pro Gln Trp Lys Ser Glu Ser Leu Cys Thr Pro Gly Cys Val Thr Gly Ala
                 1   2   3   4   5   6   7   8   9   10  11  12  13  14  15
```

FIG. 2A

```
C--  --G  ---  --A  ---  --T  --G  ---  --G  ---  --A  --C  --T  ---  ---  ---            480
TTG  CAA  ACT  TGC  TTC  CTT  CAA  ACA  CTA  ACT  TGT  AAC  TGC  AAA  ATC  TCT  AAA  TAA  GTA  AAA
Leu  Gln  Thr  Cys  Phe  Leu  Gln  Thr  Leu  Thr  Cys  Asn  Cys  Lys  Ile  Ser  Lys
 16   17   18   19   20   21   22   23   24   25   26   27   28   29   30   31   32

492                      504                      516                      528                      540
CCA  TTA  GCA  TCA  CCT  TGC  TCT  GAC  TCC  TTG  CAC  TTC  TGA  GTG  TTA  TAC  ATA  CTT  ATT  TTC 552                      564                                               (terminator)
ATA  GAG  TCG  GGA  CAA  GAA  AAT  GAA  GTA  AAA  AAC  GAC  GGG  TGT  GAA  AGA  GTT  TAT  ATT  CAC
                                                                                         648
             612                      624                      636
ACC  CGT  TTT  TAT  ATT  CGG  CTT  TAA  GGA  GGA  ACA  CAA  TTG  TAG  AAC  GGA  AGA  ACG  GTT  ATT 672                      684                      696                      708                      720
TTC  GAT  CAT  GCG  TTT  TGA  ATA  ACA  TTC  CAA  TAA  TTC  CAG  TCT  CTT  CCT  CAA  ATG  CAG 732                      744                      756                      768                      780
ACA  AAG  GAT  GAA  GGA  CTT  AAG  GGT  ACT  TAC  CAG  GTT  TTA  TGG  TTA  AGA  ATA  TTT  CTA  AGA 792                      804                      816                      828
ACA  TCA  TAT  TTT  TTA  TTA  GGA  AAT  TAA  TAA  ATG  AGA  TTG  ATC  ACT  CTA  GA
```

FIG. 2B

```
                                                         12                   24                   36                   48                   60
AGTTGACGAATATTTAATAATTTTATTAATATCTTGATTTTCTAGTTCCTGAATAATATA 72                   84                   96                  108                  120
GAGATAGGTTTATTGAGTCTTAGACATACTTGAATGACCTAGTCTTATAACTATACTGAC 132                  144                  156                  168                  180
AATAGAAACATTAACAAATCTAAAACAGTCTTAATTCTATCTTGAGAAGTATTGGTAAT 192                  204                  216                  228                  240
AATATTATTGTCGATAACGCGAGCATAATAAACGGCTCTGATTAAATTCTGAAGTTTGTT

252     *    <--5' end of nisin mRNA                                            288    ***
AGATACAATGATTTCGTTCGAAGGAACTACAAAATAAATTATAAGGAGGCACTCAAAATG
                                                                                                    r.b.s.                                     MET

##############################################################

***********
AGTACAAAGATTTTAACTTGGATTTGGTATCTGTTTCGAAGAAAGATTCAGGTGCATCA
SerThrLysAspPheAsnLeuAspLeuValSerValSerLysLysAspSerGlyAlaSer
                  1   2   3   4   5   6   7   8   9  10  11  12  13  14  15  16  17  18

########--TC----C--T-TG--C-----G--C---C-----------C
        --C---TC----C--T-TG--C-----G--C---C-----------C
CCACGCATTACAAGTATTTCGCTATGTACACCCGGTTGTAAAACAGGAGCTCTGATGGGT
ProArgIleThrSerIleSerLeuCysThrProGlyCysLysThrGlyAlaLeuMETGly
  1   2   3   4   5   6   7   8   9  10  11  12  13  14  15  16  17  18

20-mer
 --C---T-------T--A--C------CTC----C--T--GTCT---                 480
 --C---T-------T--A--C------CTC----C--T--GTCT---
TGTAACATGAAAACAGCAACTTGTCATTGTAGTATTCACGTAAGCAAATAACCAAATCAA
CysAsnMETLysThrAlaThrCysHisCysSerIleHisValSerLysTER
 19  20  21  22  23  24  25  26  27  28  29  30  31  32  33  34

492  3' end of nisin mRNA -->
AGGATAGTATTTGTTAGTTCAGACATGGATACTATCC
```

FIG. 3

```
                                           ↓
                                   xba I
     r.b.s.    BstEII               C  A
TGAAAGGAGGTCACCAATATGTCAAAGTTCGATGATTTCGATTTGGATGTTGTGAAAGTCTCTAAACAA
                 METSerLysPheAspAspPheAspLeuAspValValLysValSerLysGln Bst BI                  IleAla        Sma I
       T  G                  ATTGCA         C  G
GACTCAAAAATCACTCCGCAATGGAAAAGTGAATCACTTTGTACACCAGGATGTGTAACTGGTGCATTG
AspSerLysIleThrProGlnTrpLysSerGluSerLeuCysThrProGlyCysValThrGlyAlaLeu
              1   2   3   4   5   6   7   8   9  10 11 12 13 14 15 16

Bst EII  Sna BI
                                                  G  CC   TACG
CAAACTTGCTTCCTTCAAACACTAACTTGTAACTGCAAAATCTCTAAATAAGTAAAA CCATTAGCATCA
GlnThrCysPheLeuGlnThrLeuThrCysAsnCysLysIleSerLysTer
17  18  19  20 21  22  23  24 25  26  27  28 29 30 31  32

CCTTGCTCTGACTCCTTGCACTTCTGAGTGTTATACATACTTATTTTCATAGAGTCGGGACAAGAAAATGA terminator
AGTAAAAAAACGACGGGTGTGAAAGAGTTTATATTCACACCCGTTTTTATATTCGGCTTTAAGGAGGAACAC
AATTGTAGAACGGAAGAACGGTTATTTTCGATCATGCGTTTTGAATAACATTCCAATAAAAATTCCAGTCT
CTTCCTCAAATGCAGACAAAGGATGAAGGACTTAAGGGTACTTACCAGGTTTTATGGTTAAGAATATTTCT
AAGAACATCATATTTTTTATTAGGAAATTAATAAATGAGATTGATCACTCTAGA
                                                  Xbol Mutagenic Oligonucleotides
BstEII - BstBI Fragment
    Isolated from plasmid pGHF374

BstBI - SmaI Fragment
     Eco RI       Bst BI
1  TGAATTCAGATTCGAAAATCACTCCGCAATGGAAAAGT  ----> Klenow
         Klenow  <----  GGCGTTACCTTTTCACTTAGTGAAACATGTGGGCCCAACTTCGAAACCA 2
                                   Glu        Xma I   Hind III
                                   Ile        Sma I
                         GGCGTTACCTTTTCATAAAGTGAAACATGTGGGCCCAACTTCGAAACCA 2E41
                         GGCGTTACCTTTTCATAACGTGAAACATGTGGGCCCAACTTCGAAACCA 2E41
                                  IleAla                              DHA5A
```

FIG.9A

Smal – BstEII Fragment
```
                    Xma I
    Eco RI         Sma I
3 AGAATTCACACCCGGGTGTGTAACTGGTGCATTGCAAACTTG     ----> PCR
                 ACACATTGACCACGTAACGTTTGAACGAAGGAAGTTT-------------
   ---CATGTGGTCCT/
                                                /AGTAAAACCA-----
   ------------AAACACACTAACTTGTAACTGCAAAATCTCTAAATA
         PCR <----    GAACATTGACGTTTTAGAGATTTATCCATTGGGGTTTCGAAAGTG 4
                                                  Bst EII  Hind III
```

BstEII – Xbal Fragment
```
     Eco RI         Bst EII Sna BI
5 GGAATTCATAGGTAACC TACGTAGCATCACCTTGCTCTGACTCCTTGC  ----> PCR
                   CGTAGTGGAACGAGACTGAGGAACGTGAAGA---------------
        CATTTTGGTAAT/
                                              /TCTAGA-------
   -------------ATATTTTTTATTAGGAAATTAATAAATGAGATTGATCAC
          PCR <----    CCTTTAATTATTTACTCTAACTAGTGAGATCTAACTTCGAAGACG 6
                                                     Xba I  Hind III
```

FIG.9B

LEADER SEQUENCE INDUCING A POST-TRANSLATIONAL MODIFICATION OF POLYPEPTIDES IN BACTERIA GENE THEREFOR AND SUBTILIN VARIANT OF ENHANCED STABILITY AND ACTIVITY This application is a continuation of application Ser. No. 08/220,033, filed Mar. 30 1994, now U.S. Pat. No. 5,576,420, which is a division of application Ser. No. 07/981,525, filed Nov. 25, 1992, now U.S. Pat. No. 5,516,682, which is a continuation-in-part application of U.S. patent application Ser. No. 07/214,959, filed Jul. 5, 1988, now U.S. Pat. No. 5,218,101.

BACKGROUND OF THE INVENTION

1. Field of the Invention

This invention pertains to the expression of proteins which require post-translational modification of their amino acid sequence before a mature form is reached. Such proteins exhibit amino acids other than the 20 common amino acids coded for by the conventional nucleic acids. Specifically, a leader peptide sequence is identified which can induce post-translational modification of specific amino acids when expressed in conjunction with the precursor polypeptide. Methods of forming improved compositions using this leader sequence are also addressed.

This invention also pertains to a method of converting nonbacteriocin expressing Bacillus strains to bacteriocin expressing Bacillus strains, and to mutant forms of subtilin produced by that method. Specifically, a form of subtilin having enhanced stability and activity is addressed, together with the gene therefor, and expression vehicles for that gene.

2. Discussion of the Background

Polypeptides, including those having natural antibiotic activities, have been identified which comprise amino acids other than the 20 common acids specified by the genetic code, as the expression products of bacteria, and other organisms. The structure of two of the more important ones, nisin and subtilin, are set forth in FIG. 1 of this application.

The presence in these polypeptides, and others, of the unusual amino acids lanthionine, β-methyllanthionine, D-alanine, dehydroalanine and dehydrobutyrine clearly suggests that something other than ordinary protein biosynthesis directed by the genetic code is involved in the expression of the mature forms of these naturally occurring polypeptides. Nonetheless, research has demonstrated that the appearance of these polypeptides can be blocked by protein biosynthesis inhibitors. Hurst et al., Canadian Journal of Microbiology, 17, 1379–1384 (1971). It is also known that precursor peptides of the mature forms can be detected with antibodies against the mature peptide. Nishio et al., Biochemistry Biophysics Research Community, 116, 751 (1983). These observations, with other observations concerning nisin, subtilin and related proteins suggest a mechanism that involves primary biosynthesis of a precursor via a ribosomal mechanism, followed by post-translational modifications.

The activity of these proteins, and potential mutant variations thereof, are of sufficient commercial interest so as to generate substantial activity in the field of derived microorganisms containing foreign DNA fragments and coding for the protein's production. U.S. Pat. No. 4,716,115, issued to Gonzalez et al. is directed to just such a derived microorganism. However, the impossibility of obtaining a genetic sequence that codes directly for the mature protein, and the lack of information concerning the nature of the post-translational modification necessary to arrive at the mature protein, has prohibited the cloning of microorganisms containing the specific gene which encodes for these proteins, and perhaps more importantly, has frustrated attempts to produce random variants and site-specific mutated proteins, which quite probably can be arrived at having higher degrees of activity, or other enhanced properties.

Thus, it remains an object of the biotechnology field to arrive at a comprehensive understanding of the mechanism by which the mature forms of these unusual amino acid-containing polypeptides are made, and to develop an expression vehicle for incorporating a gene which will specifically encode for the production of these peptides and which is suitable for the transformation of commonly available bacteria.

In application Ser. No. 07/214,959 (now U.S. Pat. No. 5,218,101), the polypeptide precursors for expression of mature subtilin and nisin, and corresponding gene sequences, are disclosed. As related in this application, these bacteriocins are of particular interest in that they contain unusual amino acids that are introduced subsequent to nucleic acid translation, presumably by specific enzyme mechanisms contained within the cell, and possibly on the ribosome. Thus, this application identifies the gene and amino acid leader sequence necessary for the expression of the polypeptide precursor which, upon undergoing post-translational modification, results in the expression of the mature bacteriocin.

While these two antibiotics share considerable structural homology, as discussed in application Ser. No. 07/214,959, now U.S. Pat. No. 5,218,101, they are quite distinct in certain chemical properties. Of particular importance is the tendency of the subtilins to undergo spontaneous inactivation at a substantially greater rate than that exhibited by nisin. In aqueous solution at pH 6.8, spontaneous inactivation is accompanied by chemical modification of the dehydroalanine at position 5 of the mature bacteriocin, with a kinetic first-order $t_{1/2}$ of 0.8 days. It is noted that the amino acid in the four position, Glu, bares an R-group on its carboxyl moiety, which may participate in the chemical modification of the adjacent amino acid residue.

Thus, nisin, which is resistant to inactivation at low pH and high temperatures, Hurst, Advanced Application of Microbiology, volume 27, pages 85–123 (1981) is widely used as a food preservative, Hurst, supra as well as Jay, Food Microbiology, vol. 8, pages 117–143 (1983) and a treatment for bacterial infections, Sears et al, Journal of Diary Science 74, page 203 (1991). In contrast, subtilin's instability renders it of little practical value, despite having a broad spectrum of action. Jay, supra.

It is clearly a desire of those of skill in the art to obtain a mature form of subtilin which is resistant to inactivation and exhibits reasonable activity, to provide an antibiotic with the potential utility of nisin. This is particularly important in light of the increasing antibiotic resistance observed among microbial populations due to the widespread use of existing antibiotics. It is further desirable of producing subtilin forms from a Bacillus host to obtain improvements in yield, and take advantage of developments.

SUMMARY OF THE INVENTION

The Applicants have identified gene leader sequences, which, when coupled with the gene encoding the precursor of a polypeptide, induces or participates in the post-translational modification of the precursor to obtain the mature form. The structure of the full gene, including probable ribosomal binding sites, confirms the post-translational modification model for the manufacture of these peptides.

The gene for the expression of the precursor, and ultimately, the mature protein, of subtilin appears in FIG. 2. The leader sequence, which can be used to promote post-translational modification of other proteins which contain unusual amino acids, such as resin and the like, is set forth specifically in FIG. 3. A separate leader sequence, bearing significant homology with that for subtilin, is also identified, and the overall gene sequence is given in FIG. 3.

Further, a mutant subtilin of enhanced stability and increased specific activity has the amino acid sequence of native mature subtilin, saved for the substitution at the four position of isoleucine for the glutamate of native, naturally occurring subtilin. This substitution results in a 57-fold increase in chemical and biological stability, as well as a 3–4 fold increase in specific activity. Apparently, the glutamate carboxyl moiety participates in the chemical modification of the dehydroalanine at position 5, but the isoleucine does not induce that modification, thus enhancing the stability of the dehydroalanine moiety at position 5. The three to four-fold increase is totally unpredicted.

BRIEF DESCRIPTION OF THE DRAWINGS

FIG. 2 is the genetic base pair sequence for the entire digested fragment containing the gene which encodes for the subtilin precursor peptide, including the leader fragment responsible for inducing post-translational modification. A putative ribosomal binding site is labeled R.B.S., the leader fragment has asterisks above it, and those amino acids of the precursor which undergo modification are set forth in bold face.

FIG. 3 is an illustration giving the sequence for the gene coding for nisin, and the precursor polypeptide corresponding thereto bearing the same types of markings and having the same meanings as FIG. 2.

Figure 6:
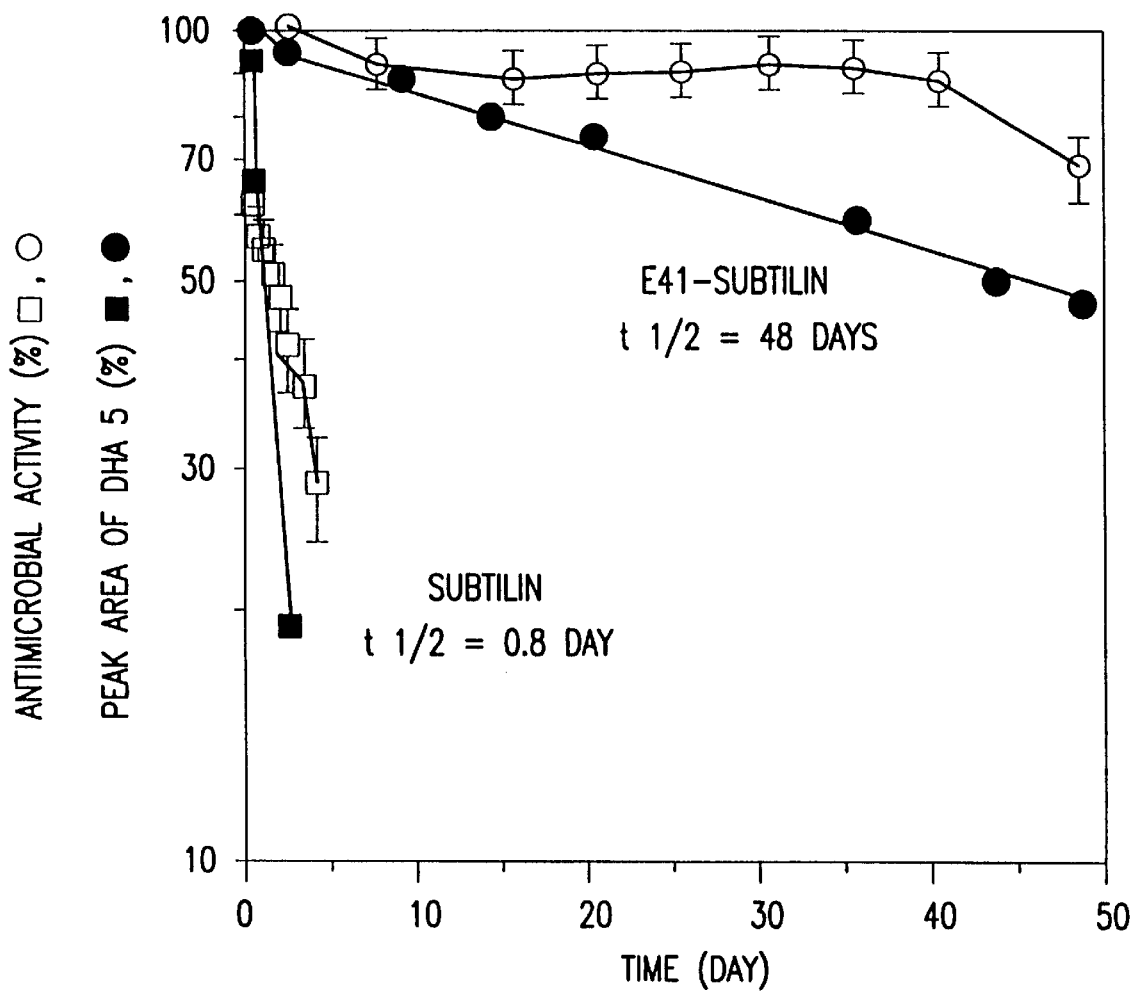

The graph of FIG. 6 compares the disappearance of the $DHA_5$ resonance peak and proton NMR spectra of natural subtilin and the E4I-subtilin mutant.

Figure 7:
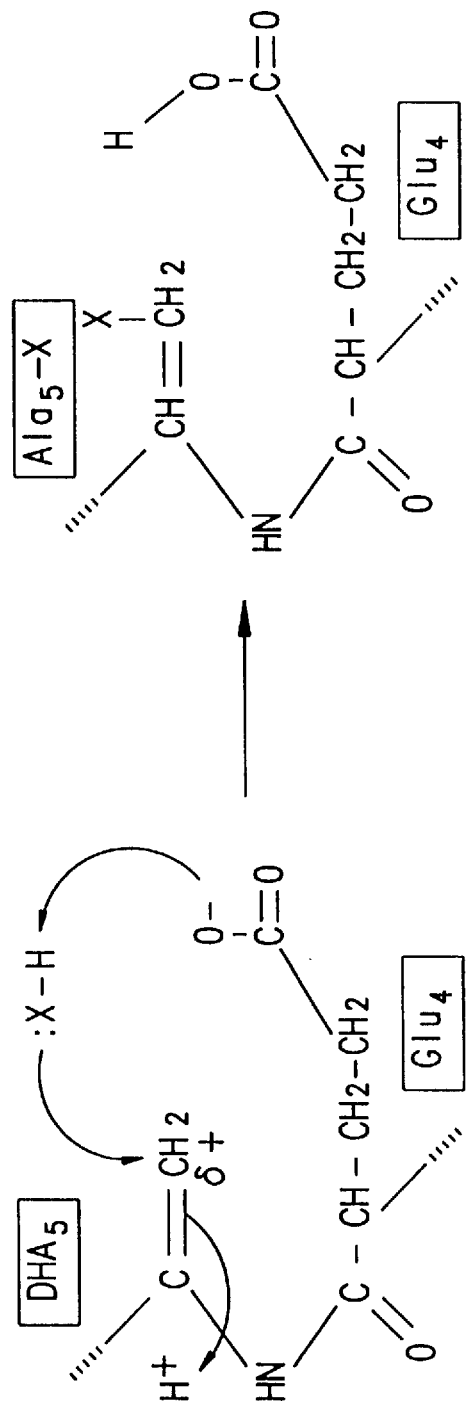

FIG. 7 illustrates a hypothetical mechanism for the modification of the $DHA_5$ residue of subtilin as assisted by the carboxyl moiety of the $Glu_4$ residue of native subtilin.

Figure 8:
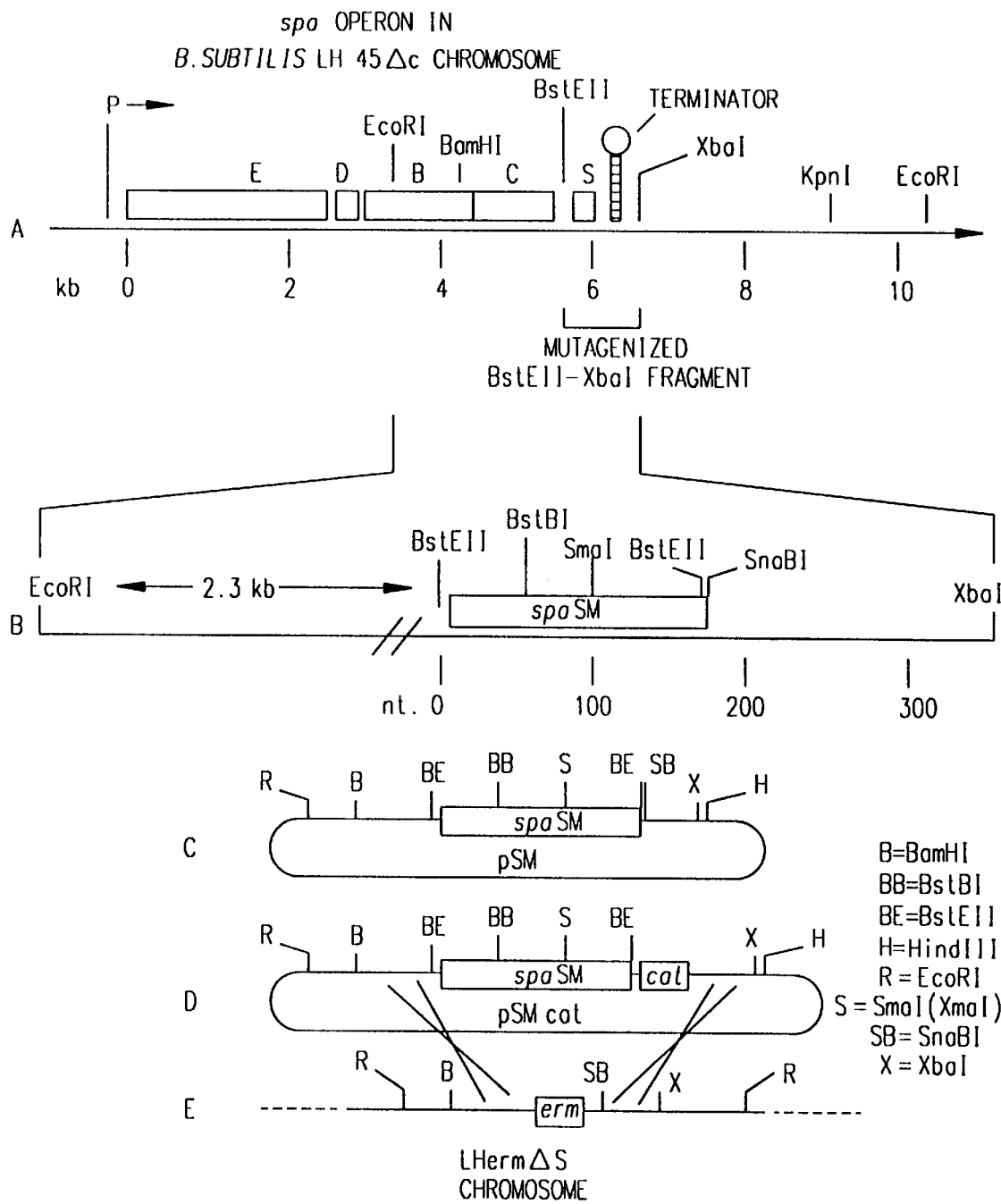

FIG. 8 is an illustration of the spa operon in the host-vector pair used for mutagenesis and replacement of the chromosomal subtilin gene with the mutant subtilin gene.

FIG. 9 is an illustration of the mutagenesis of the BstEII-XbaI restriction fragment employed in the claimed invention. The wild-type sequence contains the subtilin structural gene. The nucleotide changes, shown above the sequence along with the name of the resulting restriction site (SEQ ID NO:3), are made of silent codons that do not alter the translation product of the gene.

Figure 10:
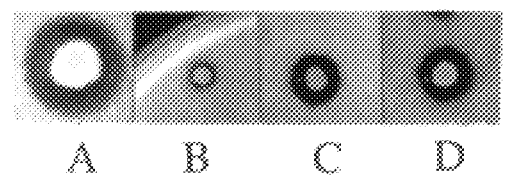

FIG. 10 is an illustration of a representative halo assay of colonies producing both subtilin and the E4I-subtilin mutant.

Figure 11A:
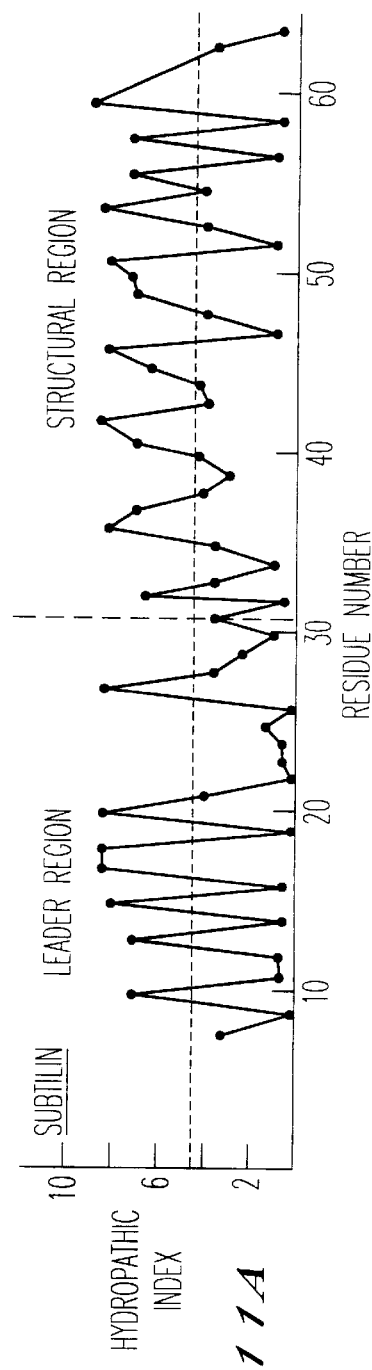
Figure 11B:
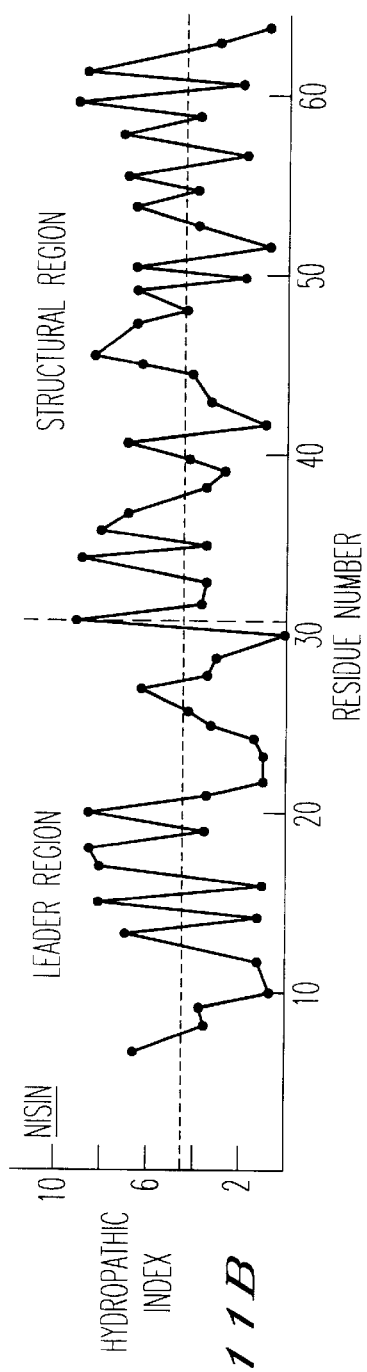
Figure 11C:
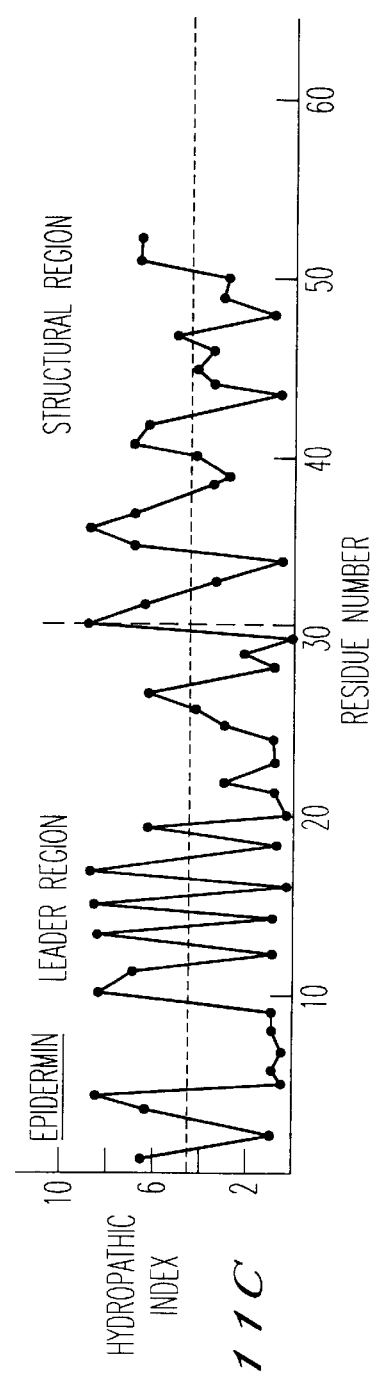

FIGS. 11A–11C are graphical representations of the relationship between hydropathic index and residue numbers of both the leader and structure region for each of subtilin, nisin and epidermin.

DETAILED DESCRIPTION OF THE INVENTION

To arrive at the gene for the polypeptide precursor for the proteins of interest, and therefore, for the ultimate expression of the mature form of the protein, it is necessary to develop a gene probe, based on the putative amino acid precursor sequence of the protein in question. For ease of discussion, the description herein will be first in the context of the gene and precursor for subtilin, although the same methodology has been employed to determine the full gene for the precursor of nisin, as is discussed subsequently and is applicable to additional genes encoding proteins containing similarly unusual amino acids in the mature form as well.

SUBTILIN

Organism and culture conditions. *Bacillus subtilis* ATCC 6633, a subtilin-producing strain, was obtained from the American Type Culture Collection, Rockville, Md. It was cultured in the high-sucrose Medium A of Nishio et al (1983), originally described by Feeney et al (1948). It contains (per L) 100 g sucrose, 11.7 g citric acid, 4 g $Na_2SO_4$, 4.2 g $(NH_4)_2HPO_4$, 5 g yeast extract (Difco), 100 ml of a salt mixture (7.62 g KCl, 4.18 g $MlgCl_2.6H_2O$, 0.543 g $MnCl_2.4H_2O$), 0.49 g $FeCl_3.6H_2O$, and 0.208 g $ZnCl_2$ in 1000 ml of $H_2O$), and sufficient $NH_4OH$ to bring the pH to 6.8–6.9 per liter. Stocks were maintained on LB plates (10 g tryptone, 5 g yeast extract, 10 g NaCl per L) containing 1.5% agar.

Clone isolation and hybridization procedures. A subtilin gene probe was designed based on the putative amino acid precursor sequence of subtilin. The nature subtilin molecule contains only 32 amino acids, and does not contain any regions of low codon degeneracy. Therefore, instead of preparing a probe mixture which contained all possible sequences encoding a short stretch of amino acids in the subtilin precursor, a single long probe was synthesized according to the strategy of Lathe, Journal of Molecular Biology, 183, pp. 1–12 (1985). Ambiguous positions within codons were chosen by educated guess, according to a codon frequency usage table constructed from the known *B. subtilis* gene which codes for alpha-amylase. Yang et al, Nucleic Acids Research, 11, pp. 237–249 (1983). Because one cannot predict the sequence homology between the probe and the target gene sequence, hybridization and wash conditions must be optimized empirically. The 96-mer "guessmer" was end-labeled using polynucleotide kinase, purified on disulfide cross-linked BAC gels as described by Hansen et al (1982), and hybridized to EcoRI digests of total ATCC 6633 genomic DNA at 7° C. temperature intervals in the range of 37°–60° C., using a 6× Standard Saline Citrate (SSC) salt strength. Separate strips were then washed, using temperature increments of 4° C., in 2× SSC. The hybridization and wash conditions that gave the best combination of signal strength and specificity were chosen for subsequent screening or a partial MboI library of ATCC 6633 DNA constructed in lambda J1. Hybridizations in which probe and target were highly homologous were carried out in the same hybridization buffer as above, but the hybridization temperature was 70° C., washes were done in 0.1× SSC at 52° C. DNA sequence analysis was done using the modified T7 polymerase "Sequenase" system supplied by United States Biochemical Corp.

RNA isolation and S1-mapping. Total RNA was isolated using the method of Ulmanen et al (1985). S1-mapping was performed by the method of Davis et al (1986), in which a synthetic oligonucleotide is used to prime second strand synthesis using single-strand M13 DNA which contains the cloned gene as template. Label was incorporated as $^{32}$p from [alpha-$^{32}$P-dATP]. After a short labeling time, an excess of unlabeled dATP was added, and second strand synthesis was continued toward completion. An appropriate restriction enzyme was used to cut the double-stranded product, and the labeled strand was obtained by electrophoresis on a denaturing agarose gel, followed by autoradiography to locate the fragment, excision of the gel, and electroelution of the DNA. After electroelution, the DNA was extracted with 1:1 chloroform:phenol and precipitated with ethanol. The labeled fragment was hybridized to total mRNA at several different temperatures, and unhybridized single-strand nucleic acid was degraded using nuclease-S1. The product was electrophoresed on a denaturing sequencing gel alongside a set of dideoxy sequencing reactions generated using the same synthetic oligonucleotide as primer. The location of the protected labeled DNA fragment with respect to the sequencing lanes identified the end of the mRNA.

RNA and protein analysis. Northern analysis was done by electroblotting acrylamide gels of RNA preparations onto Zeta-probe nylon membrane (Bio-Rad). Proteins were analyzed by electrophoresis on the polyacrylamide gel system of Swank and Munkres (1971), and silver-strained using Bio-Rad reagents. Subtilin activity was measured as for nisin, described by Morris et al (1984).

Using the above materials and methods, fragments which contained the sequence hybridizing with the guessmer were cloned into M13 and sequenced. The sequence was searched for homology to the subtilis gene probe, and also computer-translated in all reading frames. These were searched for the putative subtilin precursor sequence. A perfect match was found, which contains the exact sequence of 32 residues. The sequence is set forth in FIG. 3.

As noted, this sequence includes a portion encoding a precursor polypeptide, which contains serines, threonines and cysteines which undergo modification after translation, to arrive at the mature protein, having the unusual amino acids noted. The (−10) region corresponds closely to a consensus prokaryotic promoter (TATAAT) as observed in other bacteria, Siebenlist et al., Cell, 20, pages 269–281 (1980). The putative ribosome binding site is labeled as RBS and encompasses a 12 base pair sequence that is typical of those observed in B. subtilis, as reported by Band et al., DNA, 3, pages 17–21 (1984). It should be noted that it is positioned so that translation initiation would begin at the immediate downstream Met codon, which initiates the leader sequence of this invention. It should be noted that the subtilin precursor peptide leader region, which plays a role in the transport of subtilin outside the cell, is unusual in comparison to sequences of other prokaryotic exported proteins.

NISIN

The above approach has been duplicated for the antibiotic nisin, and the resulting gene sequence coding for the precursor is set forth in FIG. 3 attached hereto.

Bacterial strains, cloning vectors, and culture conditions. Nisin-producing Streptococcus lactis ATCC 11454 was obtained from the American Type Culture Collection (Rockville, Md.). Strains were stored at −20° C. in ATCC Medium 17 (100 g skim milk powder, 100 g tomato juice, 5 g yeast extract to pH 7.0) containing 25% glycerol. Working stocks were maintained on 1.2% LB agar plates (10 g Bacto-tryptone, 5 g Bacto-yeast extract, 10 g NaCl per liter). M17 culture medium (8), consisting of 5 g Bacto-peptone (Difco), 5 g Bacto-soytone (Difco), 2.5 g yeast extract (Difco), 5 g beef extract (Difco), 0.5 g ascorbic acid, 5 g lactose (or glucose) 19 g beta-disodium glycerophosphate (Eastman), and 0.12 g anhydrous $MgSO_4$ per liter, was used to culture S. lactis for nisin production, genomic library construction, and total RNA isolation. The organism was grown at 32° C. without aeration using a 2% inoculum into an appropriate volume of M17 medium.

Bacillus cereus T spores used in the assay for nisin production were prepared and stored as described in the art. Antibiotic activity assays were performed as previously described using fractions of the S. lactis culture supernatant.

DNA isolation procedure. S. lactis ATCC 11454 was incubated in 500 ml of M17 medium for 30 hours at 32° C. without aeration. Cells were collected by centrifugation, and washed in 25 ml PBS (8 g NaCl, 1.4 g $Na_2HPO_4$, 1.2 ml 1N HCl per liter). The cells were resuspended in 15 ml 50 mM Tris-HCl (pH 7.6) and subsequently digested with 33 micrograms per ml mutanolysin (Sigma) for 15 minutes at 37° C. with gentle agitation (12). Then 5 ml of STEP solution (13) (0.5% SDS, 50 mM Tris-HCl in 0.4M EDTA, and 1 mg per ml proteinase K) was added and incubation performed at 37° C. for 30 min with occasional mixing. The mixture was extracted with 1 volume of $CHCl_3$, 1 volume 50:50 phenol:$CHCl_3$, and finally with 1 volume $CHCl_3$. One-tenth volume 3M Na acetate and 2 volumes ethanol added; the DNA was spooled, and resuspended in 20 ml 50 mM Tris-HCl and 4 mM EDTA containing 50 micrograms per ml of pancreatic RNase (Sigma). The solution was dialyzed against a buffer of 50 mM Tris-HCl and 4 mM EDTA for 16 hours at 4° C. with one buffer change. The DNA was ethanol-precipitated two times in the presence of 2.5M ammonium acetate and finally dissolved in 2 ml 10 mM Tris-HCl, pH 7.6.

Probe construction, radiolabeling, and hybridization procedures. Several different probes were used to search for the nisin gene in S. lactis ATCC 11454 DNA. Hybridization conditions were optimized as previously described (2). Two oligomeric probes were prepared by chemical synthesis using a Biosearch Model 8700 DNA synthesizer. One was a 20-mer mixed probe designed against a region of low codon degeneracy within the putative nisin precursor sequence. The second is a single sequence 103-mer oligonucleotide probe designed using the strategy of Lathe. A natural DNA probe was also employed, which was a 1.1 kb restriction fragment containing the subtilin gene that had previously been cloned from Bacillus subtilis ATCC 6633 (2).

Library construction and isolation of the nisin gene. A total genomic library of S. lactis ATCC 11454 DNA in lambda J1 was constructed and screened as described above. Positive clones were mapped by restriction analysis and subcloned into pUC9 and pTZ19U plasmid vectors for further analysis, and into M13mp18 and M13mp18 for sequencing. Sequence determination was performed by the dideoxy termination method using modified T7 polymerase and the protocol in a Sequenase kit obtained from the United States Biochemical Company.

RNA isolation and Northern blot analysis. Total RNA isolation was performed according to the method of Ulmanen et al. RNA fractionation was performed an a denaturing acrylamide gel, electroblotted onto a Zeta-probe (Bio-Rad) nylon membrane, and hybridized as described above.

Protein analysis. Proteins were analyzed by electrophoresis on the polyacrylamide gel system of Swank and Munkres, and silver-stained using Bio-Rad reagents. Nisin activity was determined by the method of Morris et al.

Discussion

Thus, the mode by which subtilin, nisin, and other proteins containing unusual amino acids not encoded by the genetic code is established. Specific leader sequences encoded within the genes for subtilin and nisin shown in FIGS. 2 and 3 required for post-translational modification of specific amino acids, including precursor residues Ser, Thr and Cys, which are converted to the unusual amino acids referred above, undergoing reactions which include dehydration, and potential electrophilic addition reactions involving stereoinversion to generate thioether crosslinkages and D-amino acids. Genes coding for the precursor polypeptide, including the leader, can be inserted through conventional technologies into any expression vehicle, which, e.g., for nisin, include Streptococcus lactis as a natural producer, and the expression bacteria set forth, e.g., in U.S. Pat. No. 4,716,115. Similar expression vehicles can be identified for other proteins.

Subsequent to the invention addressed herein, the gene sequence for epidermin, another lanthionine-containing polypeptide antibiotic, was published by Schnell et al, Nature, 333, pp. 276–278 (1988). Although the amino acid residues of the leader sequences for the three antibiotics reflect sufficient homology to indicate a common evolutionary origin, it is clear that at this time, there are significant differences in the amino acid sequences of each, and in their corresponding gene sequences. However, as reflected in Table 1, the hydropathic index of the three leader amino acid sequences are astonishingly similar. Specifically, adjacent to the structural regions, there is a region of high hydrophilicity, followed by a region more distal from the structural region, which, on average, is neutral, but tends to alternate between a hydrophilic and a hydrophobic residue. Indeed, placed on the same graph, there is an amazing correlation with regard to these residues. This correlation continues down to the fact that each leader region reflects an interruption in the hydrophilic residues with one hydrophobic residue, at the exact same location in each case. Thus, the invention herein embraces not only the recognition that modification is accomplished by encoding a leader region which directs or aids in achieving modification in the structural region, but extends to the recognition that the leader region can be generally characterized as having a portion proximal to the structural region which is hydrophilic in nature, complemented by a more distal portion wherein hydrophilic and hydrophobic residues alternate to give an overall neutral value. Empirically, the three examples set forth herein all include the presence of a single hydrophobic residue in the hydrophilic portion adjacent the structural region. As of the filing date of application Ser. No. 07/214,959, now U.S. Pat. No. 5,278,101, it was unknown whether the presence of such a residue is essential for achieving the post-translational modifications necessary. However, given the state of skill in the art, routine experimentation can determine the necessity of such a presence, together with various alternatives, which may improve modification efficiency.

The available technology also allows the manufacture of a gene encoding a mature protein from the gene for the structural region only, which in many cases can be determined in a relatively straightforward manner, i.e., prediction based on the amino acid sequence followed by hybridization and sequence analysis. The effect of the leader sequence of this invention on specific amino acids also provides a novel means for achieving site-specific mutagenesis without resort to DNA modification. Thus, for example, it has been reported that deletion or replacement of various residues, such as cysteine, may improve biological activity. See, e.g., U.S. Pat. No. 4,518,584. Additionally, novel mutants of naturally-occurring peptides are quite likely to possibly exhibit higher activities, or better specificities for certain biological functions. These can now be prepared by insertion of the genetic code for the leader sequence of this invention in front of the gene encoding the expression of a naturally-occurring polypeptide, which will then undergo the post-translational modification directed by the leader sequence, eliminating or modifying the residues in question.

It should also be noted, of course, that where it is desired to secure substantial expression of the precursor, and not the peptide itself, this can now also be achieved, by specific excision of the leader fragment from the gene encoding the peptide precursor. In the absence of the leader sequence of this invention, it is the precursor which will be expressed, without direction to undergo post-translational modification.

Another feature of the invention of this application is the capability of designing "targeted proteins," or proteins which, by virtue of the presence of the unusual amino acids dehydroalanine and dehydrobutyrine, can be covalently attached to a "target." Thus, using structural variants, which could recognize and select for specific targets, the leader fragment can be employed to induce "binding sites," to develop a covalent bonding "antibody," to neutralize specific toxins, to select out specific material, etc. All these modifications are well within the skill of the ordinary practitioner and the expanding biotechnology arts, and so represent immediate applications of the discovery of the leader sequence disclosed herein.

Applications of this invention are not limited to the modification of existing proteins. Given current abilities to synthesize DNA sequences, specific polypeptides can be encoded by artificial clones and targeted for specific uses. As an example, given the crosslinking ability of the unusual amino acids produced through this invention, an adhesive can be prepared specific for a given substrate, e.g., carbon fibres, which due to the capability of the unusual amino acids generated by modification to form covalent linkages, can firmly bond to the substrate. The availability of amino acids allows the designer to introduce as an adhesive any desired amount of hydrophobicity, hydrophilicity, etc., to overcome problems encountered in currently used adhesives, such as epoxies.

Of course, specific applications will generate mutations of the leader sequence of this invention, and other specific variants. So long as these variants retain the essential biological function of inducing or assisting in post-translational modification, they remain within the scope of this invention.

It should be noted that a publication detailing the identification of the leader sequence by the Applicant, in conjunction with Sharmila Banerjee will appear in the Journal of Biological Chemistry, Vol. 263, proposed publication date Jul. 5, 1988.

The exact mechanism by which post-translational modification is induced is unclear. Without being bound to any theory, it is noted that the subtilin precursor exhibits residues in the leader sequence that initially alternate between high hydrophilic and high hydrophobic nature, becoming highly hydrophilic near the structural region, which, in contrast, is strongly hydrophobic. This should be contrasted with usual leader regions for exported proteins of prokaryotes, which generally have a quite hydrophobic region, and contain basic residues, riot the acidic residues of the invention. This suggests the post-translational modifications occur at a compartmentalized site, which the unusual leader sequence assists in targeting or directing the precursor to. It is expected that other proteins will participate in the modification mechanisms. Enzymes necessary to effect the essential chemical reactions localized at or near the cell membrane.

This invention has been described in specific detail with regard to specific proteins, materials and methods. Except where necessary for operability, no limitation to these specific materials is intended, nor should such a limitation be apprehended, outside the express limitations of the claims appended hereto. In particular, use of the leader sequence of this invention in conjunction with virtually any prokaryotic expression vehicle, specifically bacteria, is contemplated.

BACTERIOCIN VARIANTS

Native subtilin exhibits a dehydroalanine moiety at the 5 position ($DHA_5$). As inactivation of subtilin induced by chemical or biological environments is accompanied by modification of the $DHA_5$ moiety, with a kinetic first-order $t_{1/2}$ of 0.8 days, this modification is believed to correspond to the loss of activity in subtilin. As illustrated in FIG. 7, this chemical modification of DHAS is believed to be assisted by the carboxyl moiety of the amino acid residue of the 4 position $Glu_4$.

Notwithstanding the susceptibility of $DHA_5$ to chemical inactivation, replacement of $DHA_5$ with the corresponding amino acid alanine (retaining the hydrophobicity of the native residue while destroying the double bond) resulted in a complete loss of activity against bacterial spore outgrowth. Thus, maintenance of the $DHA_5$ moiety is a prerequisite to maintaining activity against bacterial spores.

As the glutamate of amino acid residue 4 is suspected of contributing to the inactivation of native subtilin, this moiety was converted by site-specific mutagenesis to isoleucine. The $DHA_5$ of this mutant subtilin, designated E4I-subtilin, underwent chemical modification with a $t_{1/2}$ of 48 days, 57-fold slower than native subtilin. As illustrated in FIG. 6, the rate of loss of biological activity against *Bacillus cereus* spores dropped by a similar amount.

Totally unpredicted, the specific activity of E4I-subtilin was 3–4 fold higher than natural subtilin.

The site-specific mutagenesis required to convert native subtilin to E4I-subtilin, the isolation of the same, monitoring of $DHA_5$ utility and measure of biological stability, are all detailed in the following specific examples.

Bacterial strains, cloning vectors, and culture conditions. Cloning in *Escherichia coli* was carried out by standard procedures, Maniatis et al, *Molecular Cloning: A Laboratory Manual* (1982). Transformations of competent *Bacillus subtilis* cells were performed as described, Wilson et al, *J. Bacteriol.*, 94, 562–570 and 95, 1439–1449 (1967 and 1968) as well as Young et al, *Handbook of Genetics*, Vol. 1, pp. 69–114 (1974). PAB medium is Antibiotic Medium 3 (Difco), and TBAB medium is Tryptose Blood Agar Base (Difco); plates contained 0.8% agar. Chloramphenicol and erythromycin (Sigma) were employed at 10 μg per mL.

Isolation of natural and mutant subtilin. Natural subtilin was isolated from *B. subtilis* ATCC 6633 culture supernatants by a modification of previously published procedures, Jensen and Hirschman, *Arch. Biochem.*, 4, 197–309 (1944). Cells were grown in Medium A, Bannerjee and Hansen, *J. Biol. Chem.*, 263, 9508–9514 (1988), containing 10% sucrose and incubated with good aeration for 30–35 hours at 35° C. The culture was acidified to pH 2.8 with phosphoric acid and heated in an autoclave at 121° C. for 3 min to inactivate proteases, and cooled to room temp. One-half vol of n-butanol was added, stirred at 4° C. for 2 hours, allowed to stand at 4° C. for 2 hours, and centrifuged. 2.5 volumes of acetone were added to the supernatant, allowed to stand at −20° C. for at least 2 hours, and centrifuged. Most of the pellet is subtilin, which was washed with 95% ethanol, briefly lyophilized, and dissolved in 0.1% trifluoroacetic acid. This was immediately purified by RP-HPLC as described previously for nisin (20), which employed a trifluoroacetic acid-water-acetonitrile gradient. Subtilin elutes slightly later than nisin in this gradient. Peaks were collected, lyophilized, and stored at −80° C. Subtilin that was to be subjected to proton NMR spectral analysis was dissolved in deuterated water (99.96 atom % D, Aldrich Chemical Co.) and lyophilized (repeated twice) to exchange protons. The E4I-subtilin mutant was isolated in the same way, except that the cells were grown in Medium A with 2% sucrose, and the E4I-subtilin eluted somewhat later in the HPLC gradient than natural subtilin, which reflected the fact that E4I-subtilin is slightly more hydrophobic than subtilin. It has been reported that subtilin is light-sensitive (1), so subtilin and E4I-subtilin samples were routinely protected from light. Whether E4I-subtilin is light-sensitive was not determined.

Amino acid composition analysis was performed with a Hewlett Packard (Fort Collins, CO) AminoQuant amino acid analyzer after HCl hydrolysis. N-terminal sequence analysis was performed on an Applied Biosystems (Foster City, Calif.) Model 477A peptide sequencer and Model 120A analyzer. Oligonucleotides were synthesized on a Biosearch Model 8500 oligonucleotide synthesizer.

Measurement of chemical stability of $DHA_5$. The dehydro residues of nisin and subtilin have vinyl protons that give well-separated resonances in the proton NMR spectrum, Liu and Hansen, *Appl. Environ. Microbiol.*, 56, p. 251 (1990). The areas of the vinyl proton peaks in the NMR spectrum were measured, and chemical modification of $DHA_5$ over time was taken as the decrease in peak area of the $DHA_5$ vinyl protons in subtilin and in E4I-subtilin as compared to zero time. Proton NMR spectra were obtained using a Bruker AMX-500 NMR spectrometer. The spectra were obtained at a constant temperature of 295K, using selective solvent suppression.

Measurement of biological stability of subtilin. Biological activity against *Bacillus cereus* spores was measured by a liquid assay in which various concentrations of subtilin were added to a suspension of *Bacillus cereus* T spores in 15 ml polypropylene tubes, and inhibitory effects were evaluated by phase-contrast microscopy as described previously (Morris et al, *J. Biol. Chem.*, 259, 13590–13594 (1984) and *Appl. Environ. Microbiol.*, 42, 958–962 (1981)). The amount of subtilin required to inhibit spore outgrowth during the 3 hour assay period was used as a measure of antimicrobial activity. Relative amounts of subtilin were estimated from the area of the subtilin peak (measured at 254 nm) that eluted from the C-18 analytical HPLC column during purification. The amounts were converted to molar quantities of subtilin by comparing the peak area of subtilin with that of a known molar quantity of a nisin standard (21). For this purpose, the extinction coefficients of nisin and subtilin at 254 nm were assumed to be the same, in that absorbance at this wavelength is mainly due to the same three dehydro residues present in both peptides. The biological activity against *Bacillus cereus* spores of the E4I-subtilin mutant was determined in the same way as for natural subtilin.

Figure 1:
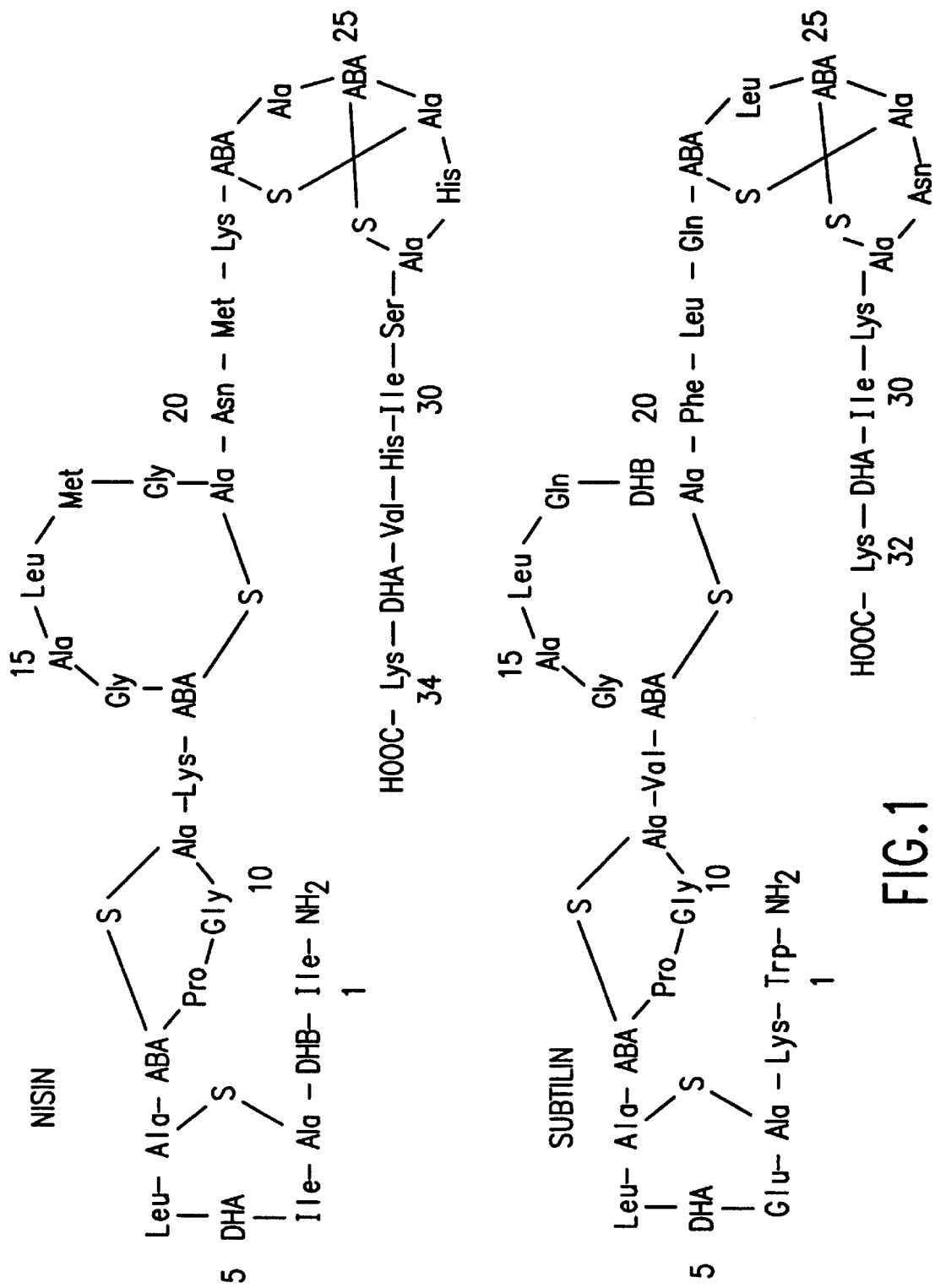
FIG. 1 is the conformational structure for the small antibiotic proteins nisin and subtilin, as determined by Gross et al., Protein Cross-linking, pages 131–153 (1977).
Figure 4:
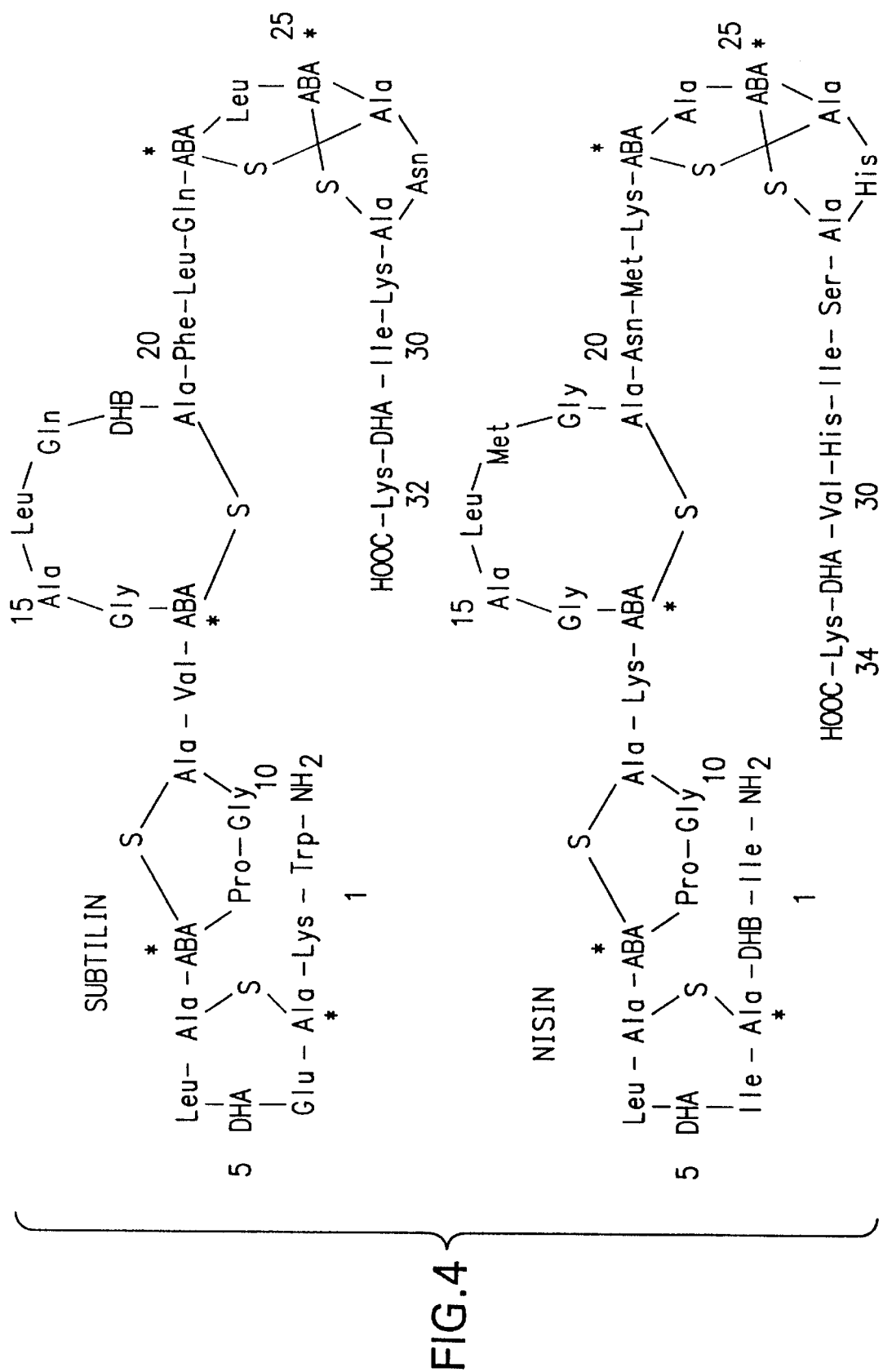
FIG. 4 is an illustration of the amino acid sequences for the bacteriocins subtilin and nisin. Asterisks indicate the amino acid has the (D)-stereo configuration at the α-carbon.
Figure 5A:
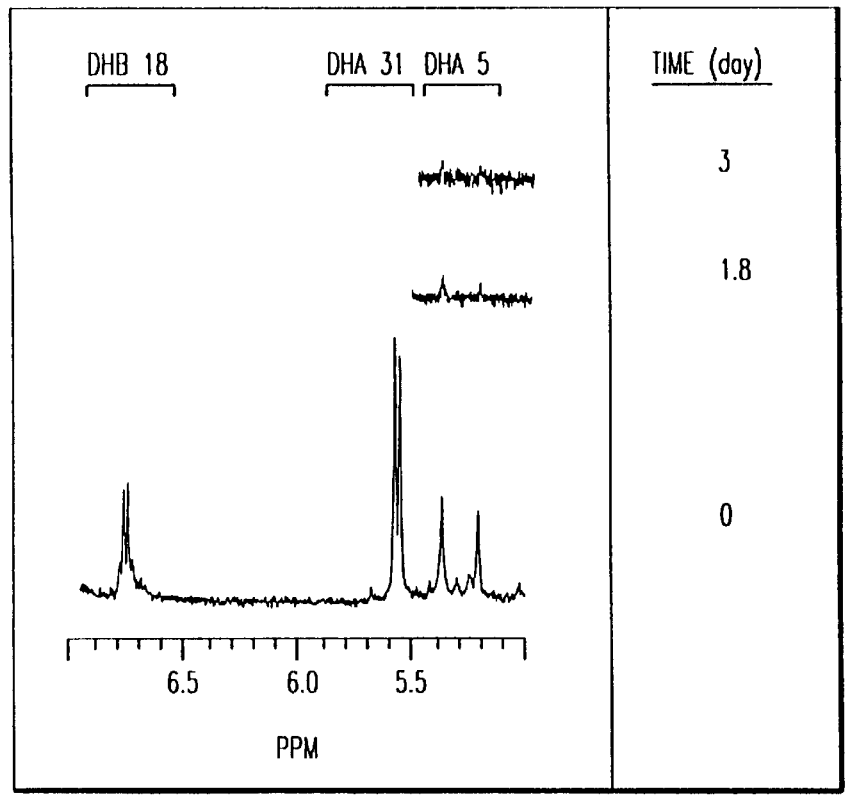
FIGS. 5A and 5B are comparative proton NMR spectra of native subtilin and E4I-subtilin, the mutant of the claimed invention.
Figure 5B:
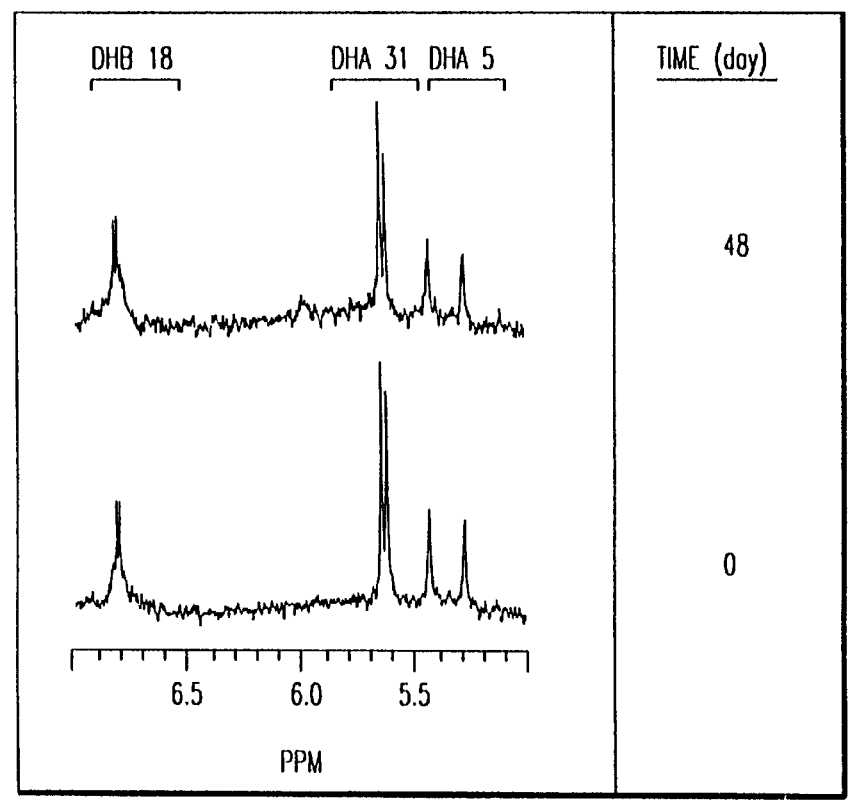

Chemical and biological stability of natural subtilin. The natural producer of subtilin is *B. subtilis* ATCC 6633. Subtilin was isolated and purified from a culture supernatant of this organism as described above. The purified subtilin was split into two samples, one of which was dissolved in $D_2O$ at pH 6.8 and subjected to proton NMR spectroscopy; and the other was dissolved in 50 mM $NaP_i$ at pH 6.8 and a portion assayed for biological activity against *Bacillus cereus* spores. These dissolved samples were incubated at room temperature, and from time to time, the NMR spectrum of the one sample and the biological activity of the other sample against *Bacillus cereus* spores were determined. The only vinyl proton peaks in the NMR spectrum that changed during incubation were those corresponding to $DHA_5$, which decreased in area over time (FIG. 5). FIG. 6 shows that the rate of disappearance of $DHA_5$ conforms to a first-order process with a $t_{1/2}$ of 0.8 days. FIG. 6 also shows that the biological activity against *Bacillus cereus* spores dropped at approximately this same rate.

Although the chemical environment of $DHA_5$ that is responsible for its reactivity could be exerted from anywhere within the peptide, it is likely that residues in the immediate vicinity of $DHA_5$ are particularly important. This focuses attention on the three residues in the vicinity of $DHA_5$ that are different. Focusing still further, the glutamate residue at position 4, which is immediately adjacent to $DHA_5$ is particularly suspicious in that a mechanism by which it could participate in the modification of $DHA_5$ exists. One possibility is that the glutamate carboxyl could directly add to the double bond of $DHA_5$. Another, perhaps more likely, mechanism is that the glutamate carboxyl could act as a general base to activate a potential nucleophile by deprotonation as shown in FIG. 7. For example, if the nucleophile were a hydroxyl ion derived by deprotonation of a water molecule, one would expect to see a first-order modification rate of $DHA_5$, as was actually observed.

A host-vector system for mutagenesis of the subtilin gene. Mutagenesis of the subtilin gene required the development of a suitable host-vector system. The gene (spas) that encodes the subtilin prepeptide is part of the spa operon in the chromosome of *Bacillus subtilis* (FIG. 8). It lies on a natural BstEII-XbaI restriction fragment whose sequence is shown in FIG. 9. The prepeptide gene is so small that it does not contain many useful restriction sites, so a sequence was engineered with changes at silent sites that would introduce new restriction sites without changing the translation product. The engineered sequence (SEQ. ID. NO:3) and the restriction sites introduced are shown in FIG. 9. The addition of these new restriction sites permits a cartridge mutagenesis approach to making mutations in the subtilin gene.

Previous attempts to express the subtilin prepeptide from a multi-copy plasmid in *Bacillus subtilis* failed, and it was concluded that mutants of the subtilin gene should be expressed by placing them in the chromosome at the site of the natural gene. If this were done by removing the natural gene before replacing it with the mutant copy, one would eliminate concern about ambiguities arising from simultaneous expression of natural and mutant copies within the same cell. The process of replacing chromosomal genes in *Bacillus subtilis* by a double-crossover between a linear plasmid and chromosomal sequences is well-established, requiring only that the plasmid contain a suitable selective marker flanked by appropriate chromosomal homologies. To achieve this, an erythromycin resistance (erm) gene was used to first replace, and thus delete, the natural chromosomal subtilin gene. The erm gene was then replaced by a mutant copy of the subtilin gene using a flanking chloramphenicol resistance (cat) gene as a selective marker, as illustrated in FIG. 8. The *B. subtilis* host cell (called LHermΔS, deposited under the terms of the Budapest Treaty at the American Type Culture Collection, Rockville, Md. 20852, U.S.A., under the ATCC Designation No. 55625) that contains the erm gene in place of the subtilin gene is also shown in FIG. 8. This LHermΔS-pSMcat host-vector pair (pSMcat has also been deposited under the terms of the Budapest Treaty at the American Type Culture Collection, Rockville, Md. 20852, U.S.A., under Designation No. 75914) has proved very versatile, and can be used to mutagenize the subtilin gene by a variety of site-directed and random strategies.

Prior to constructing a subtilin mutant, this system was tested thoroughly. The LHermΔS host, in which the natural subtilin gene had been replaced by an erm gene, was checked carefully to verify that it had erythromycin resistance, lacked the subtilin gene, and was unable to produce subtilin as established by a halo assay (FIG. 10). The engineered sequence in the pSMcat plasmid was confirmed by DNA sequence analysis, and then linearized and integrated into the LHermΔS host chromosome by a double-crossover, whereupon the host became erythromycin-sensitive and chloramphenicol-resistant, showing that replacement of the erm gene by the SMcat sequence had occurred. These cells produced normal amounts of subtilin activity (FIG. 7), showing that the silent mutations introduced into the sequence to give new restriction sites were indeed silent, and that transcription-translation of the gene was occurring normally. Southern hybridization analysis was used to show that the gene had integrated at the proper location in the chromosome.

Construction of E4I-subtilin. The E4I mutation was then introduced into the pSMcat plasmid by excising the BstBI-SmaI fragment (SEQ. ID NO:4) and replacing it with the BstBI-SmaI mutagenic fragment (SEQ. ID NO:5) to give plasmid pE4IScat, in which the $Glu_4$ codon had been replaced by an Ile codon. The fragment replacement was confirmed by DNA sequence analysis of the insert in pE4IScat. The mutagenized sequence (SEQ. ID NO:6) was then introduced into the LHermΔS host chromosome by linearizing pE4IScat, transforming it into the host, and selecting for the double-crossover replacements on chloramphenicol-PAB plates. Chloramphenicol-resistant and erythromycin-sensitive colonies were found, showing that replacement of the erm gene with the mutant subtilin gene had occurred. Several chloramphenicol-resistant colonies were selected and subjected to Southern hybridization analysis to show that the mutant subtilin gene had been integrated into the LHermΔS host. One of these colonies, called LHE4IScat, was analyzed for subtilin-like activity in a halo assay, as shown in FIG. 10. The LHE4IScat colony produced a halo, showing that the E4I-subtilin that it produces has antimicrobial activity. This colony was grown up in culture, from which the putative E4I-subtilin (SEQ. ID NO:7) was isolated and then purified by HPLC chromatography. The E4I-subtilin eluted later in the gradient, at higher concentrations of acetonitrile, than natural subtilin; which is consistent with the mutant being more hydrophobic, as would be expected. The E4I-subtilin was subjected to amino acid composition and N-terminal sequence analysis. The composition showed one more Ile and one less Glu (determined as Glx) than natural subtilin, as expected; but was otherwise identical to natural subtilin, as expected. The N-terminal sequence was Trp-Lys-(blank)-Ile (sequence blank from here on); compared to natural subtilin which gave Trp-Lys-(blank)-Glu- (sequence blank from here on).

The blank at residue 3 is expected, because the Ala remains tethered to the thioether group and is not released, Kellner et al, *Eur. J. Biochem.*, 177, 53–59 (1988) and Agnew, *Chem. Int. Ed. Engl.*, 28, 616–619 (1988), and the Edman degradation stops at residue 5 because it is unable to process a dehydro reside, Liu and Hansen, J. Bacteriol., 173, 7387–7390 (1991). The composition analysis and N-terminal sequence thus show that the E4I-subtilin prepeptide has undergone the full complement of post-translational modifications, including dehydration of all serines and all threonines, formation of all thioether cross-linkages within the structural region, and accurate removal of the leader peptide. If even one of the several dehydrations or cross-linkages had not occurred, or if the leader sequence had been inaccurately cleaved, it would have been reflected as abnormal amino acid composition, or abnormal N-terminal sequence, or both.

E4I-subtilin has enhanced specific activity. The specific activity of E4I-subtilin was measured using the spore outgrowth assay and compared to natural subtilin. E4I-subtilin showed inhibition at about 0.3 $\mu$g per ml (80 nM), whereas normal subtilin showed inhibition at about 1 $\mu$g per ml (280 nM). The mutant subtilin was accordingly 3–4 times more potent than natural subtilin in this particular biological assay. It is worth noting that natural subtilin, and especially the mutant subtilin, are effective at molar concentrations that are appreciably lower (an order of magnitude) than other common antibiotics such as ampicillin or chloramphenicol.

E4I-subtilin has enhanced chemical and biological stability. The central design strategy in the construction of a stable mutant of subtilin was based on the idea that the chemical and biological stabilities of subtilin are determined by the chemical reactivity of $DHA_5$; and that $DHA_5$ in natural subtilin is unstable because the $Glu_4$ carboxyl participates in its chemical modification (FIG. 7). This idea led to a prediction that mutation of $Glu_4$ to Ile would enhance the chemical and biological stability of subtilin because the possibility of carboxyl-group participation in the modification of $DHA_5$ would be eliminated. The chemical stability of $DHA_5$ in E4I-subtilin was accordingly evaluated by observing the disappearance over time of the $DHA_5$ vinyl proton resonance peaks in the NMR spectra, as was done for natural subtilin. FIG. 6 shows that the rate of disappearance of $DHA_5$ conforms to a first-order rate process with a $t_{1/2}$ of 48 days. This is a dramatic 57-fold increase in the stability of E4I-subtilin in comparison to natural subtilin, which had a $t_{1/2}$ of only 0.8 days. The biological stability was determined by measuring the activity over the same time course using the spore outgrowth assay. FIG. 6 shows that the activity of the mutant subtilin against *Bacillus cereus* spores dropped very little during the 48-day incubation period, showing that the biological stability was dramatically increased compared to natural subtilin. Thus, the $Glu_4$ to Ile mutation caused a dramatic enhancement of the general stability of the subtilin molecule, both in terms of the chemical stability of the $DHA_5$ residue, and its biological activity.

E4I-subtilin in which $DHA_5$ mutated to Ala has no activity against snore outgrowth. If $DHA_5$ plays a critical role in the activity of subtilin against bacterial spores, its mutation to another residue should result in a molecule that has no activity in the bacterial spore assay. It was decided that an appropriate experiment would involve mutation of the $DHA_5$ residue of E4I-subtilin to Ala (SEQ. ID NO:9). Ala was chosen in order to retain the hydrophobicity of DHAs while destroying the double bond. E4I-subtilin was chosen in lieu of subtilin because of its greater inherent stability. E4I/DHA5A-subtilin (SEQ. ID NO:10) was constructed using the mutagenic oligonucleotide shown in FIG. 9 (SEQ. ID NO:11). The mutant was isolated in the same manner as subtilin and E4I-subtilin, and subjected to the complete range of tests for correct post-translational processing, including amino acid composition analysis, N-terminal sequence analysis, and NMR spectroscopy. The results established that all the post-translational steps occurred correctly. The biological activity of the E4I/DHA5A mutant subtilin was then determined in the bacterial spore outgrowth assay. Whereas E4I-subtilin inhibited spore outgrowth at a concentration of 0.3 $\mu$g/ml, the E4I/DHA5A subtilin was devoid of inhibitory activity against outgrowing spores, even at a concentration of 50 $\mu$g/ml, which is 150-fold higher than the concentration at which E4I-subtilin inhibits. Higher concentrations were not tested. Therefore, an intact $DHA_5$ is critical for subtilin to inhibit spore outgrowth.

Accordingly, the E4I-subtilin of the claimed invention, identical to native subtilin saved for the substitution at the 4-position of an isoleucine residue in place of the naturally-occurring glutamate residue (SEQ. ID NO:7) yields an antibiotic 57-fold more stable than the natural version, with an increase in specific activity of 3–4 times the naturally expressed antibiotic. Other residues, which are inert to the deactivation of the dehydroalanine critical for activity at position 5, and which do not independently adversely affect the performance of the antibiotic, may be used to give similar results. The preparation of such analogs is a matter for empirical study which can be conducted according to the protocol set forth above.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A polypeptide sequence which, when attached as a leader to a protein precursor which undergoes post-translational modification, assists in inducing said modification, said polypeptide sequence having the biological function of the amino acid sequence of SEQ. ID NO:26: Met Ser Lys Phe Asp Asp Phe Asp Leu Asp Val Val Lys Val Ser Lys Gln Asp Ser Lys Ile Thr Pro Gln.

2. A composition, comprising a precursor polypeptide which, when expressed in bacteria, is converted after translation to subtilin.

3. The polypeptide of claim 2, wherein said polypeptide has the sequence of SEQ. ID. NO:2: Met Ser Lys Phe Asp Asp Phe Asp Leu Asp Val Val Lys Val Ser Lys Gln Asp Ser Lys Ile Thr Pro Gln Trp Lys Ser Glu Ser Leu Cys Thr Pro Gly Cys Val Thr Gly Ala Leu Gln Thr Cys Phe Leu Gln Thr Leu Thr Cys Asn Cys Lys Ile Ser Lys.

4. A polypeptide sequence which, when attached as a leader to a protein precursor which undergoes post-translational modification, assists in inducing said modification, said polypeptide sequence having the biological function of the amino acid sequence of SEQ ID NO:25: Met Ser Thr Lys Asp Phe Asn Leu Asp Leu Val Ser Val Ser Lys Lys Asp Ser Gly Ala Ser Pro Arg.

5. A composition, comprising a precursor polypeptide which, when expressed in bacteria, is converted after translation to nisin.

6. A method for inducing site-specific mutagenesis in a desired polypeptide having, as translated, at least one amino acid selected from the group consisting of Cys, Thr and Ser, comprising:

preparing a DNA fragment encoding a precursor polypeptide comprising said desired polypeptide and a leader fragment attached thereto, said leader fragment comprising a region of residues adjacent to said desired polypeptide which are predominantly hydrophilic, and a more distal region having an overall neutral hydropathic index but wherein substantially all adjacent residues have opposite hydropathic indices, and inserting said fragment in the DNA of an expression vehicle to express and modify the precursor polypeptide.

7. The method of claim 6, wherein said expression vehicle is a prokaryote.

8. The method of claim 7, wherein said expression vehicle is a bacteria.

9. A polypeptide expressed by an expression vehicle comprising at least one residue not encoded by DNA, said residue being at a predetermined site, caused by post-translational modifications of a precursor polypeptide comprising a leader fragment having a region of highly hydrophilic residues adjacent to a structural region, said leader fragment having a second region of residues of substantially alternatively hydropathic index, said structural region bearing a Cys, Ser or Thr residue at this site corresponding to said predetermined site, said polypeptide being one not encoded by a naturally occurring DNA genome of said expression vehicle.

10. A process for the expression of site directed mutants of nisin, subtilin or similar peptides, which comprises expressing site directed mutants of nisin, subtilin or similar proteins having a modification in a mature sequence and having substantially altered biological properties in a mature peptide.

11. A process for the expression of nisin or subtilin, which comprises expressing an entire structural gene for nisin or subtilin in recombinant microorganisms produced by transformation with plasmids which incorporate said entire structural genes for nisin or subtilin therein.

12. A transformed microorganism prepared from a Bacillus strain lacking expression of a mutant bacteriocin, said transformed microorganism comprising a gene for expression of a prepeptide which is transformed after translation by said microorganism into said mutant bacteriocin, said gene being inserted into the DNA of said strain via a host-vector pair which deletes a gene in said strain for expression of native bacteriocin and inserts said gene for said prepeptide in its correct reading frame at the position corresponding to that occupied by said gene for said native bacteriocin in its native DNA.

13. A method of transforming a host Bacillus strain by insertion of DNA for expression of a mutant bacteriocin prepeptide, comprising:
deleting a gene from said host strain for expression of the native form of said bacteriocin and replacing it with a marker gene giving rise to a detectable phenotype, replacing said marker gene with a gene encoding said mutant bacteriocin prepeptide in the correct reading frame at the location of said host's DNA occupied by said deleted gene.

14. A method of transforming a lanthocin-producing host strain with a gene which expresses a mutant bacteriocin prepeptide, comprising:
replacing a gene which expresses a native bacteriocin with a marker gene providing a detectable phenotype, wherein said native bacteriocin undergoes post-translational modification resulting in the presence of one or more of lanthionine, $\beta$-methyllanthionine, D-alanine, dehydroalanine or dehydrobutyrine residues in said bacteriocin; and
replacing said marker gene with said gene which expresses said mutant bacteriocin prepeptide in the correct reading frame at the location of said gene expressing the native bacteriocin.

15. A plasmid, comprising a gene encoding a polypeptide wherein, when expressed in *Bacillus subtilis*, said polypeptide is converted to an antibiotic having the amino acid sequence of native subtilin, except that the 4-position of the native sequence is substituted with isoleucine.

16. A transformed microorganism, which expresses a gene encoding a polypeptide wherein, when expressed in *Bacillus subtilis*, said polypeptide is converted to an antibiotic having the amino acid sequence of native subtilin, except that the 4-position of the native sequence is substituted with isoleucine.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
( A ) LENGTH: 545 base pairs
( B ) TYPE: nucleic acid
( C ) STRANDEDNESS: unknown
( D ) TOPOLOGY: unknown ( i i ) MOLECULE TYPE: DNA (genomic)

( v i ) ORIGINAL SOURCE:
    ( A ) ORGANISM: Bacillus subtilis ( i x ) FEATURE:
    ( A ) NAME/KEY: CDS
    ( B ) LOCATION: 19..186

( i x ) FEATURE:
    ( A ) NAME/KEY: mat_peptide
    ( B ) LOCATION: 91..186

( i x ) FEATURE:
    ( A ) NAME/KEY: protein_bind
    ( B ) LOCATION: 9..15
    ( C ) IDENTIFICATION METHOD: experimental
    ( D ) OTHER INFORMATION: /function="restriction site"
        / bound_moiety= "BstEII"
        / evidence= EXPERIMENTAL ( i x ) FEATURE:
    ( A ) NAME/KEY: protein_bind
    ( B ) LOCATION: 540..545
    ( C ) IDENTIFICATION METHOD: experimental
    ( D ) OTHER INFORMATION: /function="restriction site"
        / bound_moiety= "XbaI"
        / evidence= EXPERIMENTAL ( x i ) SEQUENCE DESCRIPTION: SEQ ID NO:1:

```
TGAAAGGAGG  TCACCAAT  ATG  TCA  AAG  TTC  GAT  GAT  TTC  GAT  TTG  GAT  GTT               51
                      Met  Ser  Lys  Phe  Asp  Asp  Phe  Asp  Leu  Asp  Val
                      -24            -20                      -15

GTG  AAA  GTC  TCT  AAA  CAA  GAC  TCA  AAA  ATC  ACT  CCG  CAA  TGG  AAA  AGT            99
Val  Lys  Val  Ser  Lys  Gln  Asp  Ser  Lys  Ile  Thr  Pro  Gln  Trp  Lys  Ser
               -10                      -5                        1

GAA  TCA  CTT  TGT  ACA  CCA  GGA  TGT  GTA  ACT  GGT  GCA  TTG  CAA  ACT  TGC           147
Glu  Ser  Leu  Cys  Thr  Pro  Gly  Cys  Val  Thr  Gly  Ala  Leu  Gln  Thr  Cys
     5                        10                      15

TTC  CTT  CAA  ACA  CTA  ACT  TGT  AAC  TGC  AAA  ATC  TCT  AAA  TAAGTAAAAC              196
Phe  Leu  Gln  Thr  Leu  Thr  Cys  Asn  Cys  Lys  Ile  Ser  Lys
20                        25                        30

CATTAGCATC  ACCTTGCTCT  GACTCCTTGC  ACTTCTGAGT  GTTATACATA  CTTATTTTCA                   256

TAGAGTCGGG  ACAAGAAAAT  GAAGTAAAAA  ACGACGGGTG  TGAAAGAGTT  TATATTCACA                   316

CCCGTTTTTA  TATTCGGCTT  TAAGGAGGAA  CACAATTGTA  GAACGGAAGA  ACGGTTATTT                   376

TCGATCATGC  GTTTTGAATA  ACATTCCAAT  AAAAATTCCA  GTCTCTTCCT  CAAATGCAGA                   436

CAAAGGATGA  AGGACTTAAG  GGTACTTACC  AGGTTTTATG  GTTAAGAATA  TTTCTAAGAA                   496

CATCATATTT  TTTATTAGGA  AATTAATAAA  TGAGATTGAT  CACTCTAGA                                 545
```

( 2 ) INFORMATION FOR SEQ ID NO:2:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ser  Lys  Phe  Asp  Asp  Phe  Asp  Leu  Asp  Val  Val  Lys  Val  Ser  Lys
-24                      -20                      -15                      -10

Gln  Asp  Ser  Lys  Ile  Thr  Pro  Gln  Trp  Lys  Ser  Glu  Ser  Leu  Cys  Thr
               -5                        1                        5

Pro  Gly  Cys  Val  Thr  Gly  Ala  Leu  Gln  Thr  Cys  Phe  Leu  Gln  Thr  Leu
          10                      15                       20
```

Thr Cys Asn Cys Lys Ile Ser Lys
25                  30

( 2 ) INFORMATION FOR SEQ ID NO:3:

( i ) SEQUENCE CHARACTERISTICS:
        ( A ) LENGTH: 545 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: protein_bind
        ( B ) LOCATION: 9..15
        ( C ) IDENTIFICATION METHOD: experimental
        ( D ) OTHER INFORMATION: /function="restriction site"
                / bound_moiety= "BstEII"
                / evidence= EXPERIMENTAL ( i x ) FEATURE:
        ( A ) NAME/KEY: protein_bind
        ( B ) LOCATION: 42..47
        ( D ) OTHER INFORMATION: /function="restriction site"
                / bound_moiety= "Xba I"

( i x ) FEATURE:
        ( A ) NAME/KEY: protein_bind
        ( B ) LOCATION: 72..78
        ( D ) OTHER INFORMATION: /function="restriction site"
                / bound_moiety= "Bst BI"

( i x ) FEATURE:
        ( A ) NAME/KEY: protein_bind
        ( B ) LOCATION: 115..120

( i x ) FEATURE:
        ( A ) NAME/KEY: protein_bind
        ( B ) LOCATION: 189..195

( i x ) FEATURE:
        ( A ) NAME/KEY: protein_bind
        ( B ) LOCATION: 196..201
        ( D ) OTHER INFORMATION: /function="restriction site"
                / bound_moiety= "Sna BI"

( i x ) FEATURE:
        ( A ) NAME/KEY: protein_bind
        ( B ) LOCATION: 540..545
        ( D ) OTHER INFORMATION: /function="restriction site"
                / bound_moiety= "XbaI"

( x i ) SEQUENCE DESCRIPTION: SEQ ID NO:3:

| | | | | | |
|---|---|---|---|---|---|
| TGAAAGGAGG | TCACCAATAT | GTCAAAGTTC | GATGATTTCG | ATCTAGATGT | TGTGAAAGTC | 60 |
| TCTAAACAAG | ATTCGAAAAT | CACTCCGCAA | TGGAAAAGTG | AATCACTTTG | TACACCCGGG | 120 |
| TGTGTAACTG | GTGCATTGCA | AACTTGCTTC | CTTCAAACAC | TAACTTGTAA | CTGCAAAATC | 180 |
| TCTAAATAGG | TAACCTACGT | AGCATCACCT | TGCTCTGACT | CCTTGCACTT | CTGAGTGTTA | 240 |
| TACATACTTA | TTTTCATAGA | GTCGGGACAA | GAAAATGAAG | TAAAAAACGA | CGGGTGTGAA | 300 |
| AGAGTTTATA | TTCACACCCG | TTTTTATATT | CGGCTTTAAG | GAGGAACACA | ATTGTAGAAC | 360 |
| GGAAGAACGG | TTATTTTCGA | TCATGCGTTT | TGAATAACAT | TCCAATAAAA | ATTCCAGTCT | 420 |
| CTTCCTCAAA | TGCAGACAAA | GGATGAAGGA | CTTAAGGGTA | CTTACCAGGT | TTTATGGTTA | 480 |
| AGAATATTTC | TAAGAACATC | ATATTTTTA | TTAGGAAATT | AATAAATGAG | ATTGATCACT | 540 |
| CTAGA | | | | | | 545 |

( 2 ) INFORMATION FOR SEQ ID NO:4:

( i ) SEQUENCE CHARACTERISTICS:
    ( A ) LENGTH: 49 base pairs
    ( B ) TYPE: nucleic acid
    ( C ) STRANDEDNESS: unknown
    ( D ) TOPOLOGY: linear ( i i ) MOLECULE TYPE: DNA (genomic)

( v i ) ORIGINAL SOURCE:
    ( A ) ORGANISM: Bacillus subtilis ( x i ) SEQUENCE DESCRIPTION: SEQ ID NO:4:

GGCGTTACCT TTTCACTTAG TGAAACATGT GGGCCCAACT TCGAAACCA     49

( 2 ) INFORMATION FOR SEQ ID NO:5:

( i ) SEQUENCE CHARACTERISTICS:
    ( A ) LENGTH: 49 base pairs
    ( B ) TYPE: nucleic acid
    ( C ) STRANDEDNESS: unknown
    ( D ) TOPOLOGY: linear ( i i ) MOLECULE TYPE: DNA (genomic)

( x i ) SEQUENCE DESCRIPTION: SEQ ID NO:5:

GGCGTTACCT TTTCATAAAG TGAAACATGT GGGCCCAACT TCGAAACCA     49

( 2 ) INFORMATION FOR SEQ ID NO:6:

( i ) SEQUENCE CHARACTERISTICS:
    ( A ) LENGTH: 545 base pairs
    ( B ) TYPE: nucleic acid
    ( C ) STRANDEDNESS: unknown
    ( D ) TOPOLOGY: unknown ( i i ) MOLECULE TYPE: DNA (genomic)

( i x ) FEATURE:
    ( A ) NAME/KEY: CDS
    ( B ) LOCATION: 19..186

( i x ) FEATURE:
    ( A ) NAME/KEY: mat_peptide
    ( B ) LOCATION: 91..186

( i x ) FEATURE:
    ( A ) NAME/KEY: protein_bind
    ( B ) LOCATION: 9..15
    ( C ) IDENTIFICATION METHOD: experimental
    ( D ) OTHER INFORMATION: /function="restriction site"
        / bound_moiety= "BstEII"
        / evidence= EXPERIMENTAL ( i x ) FEATURE:
    ( A ) NAME/KEY: protein_bind
    ( B ) LOCATION: 42..47
    ( D ) OTHER INFORMATION: /function="restriction site"
        / bound_moiety= "Xba I"

( i x ) FEATURE:
    ( A ) NAME/KEY: protein_bind
    ( B ) LOCATION: 72..78
    ( D ) OTHER INFORMATION: /function="restriction site"
        / bound_moiety= "Bst BI"

( i x ) FEATURE:
    ( A ) NAME/KEY: protein_bind
    ( B ) LOCATION: 115..120

( i x ) FEATURE:
    ( A ) NAME/KEY: protein_bind
    ( B ) LOCATION: 189..195

( i x ) FEATURE:
    ( A ) NAME/KEY: protein_bind
    ( B ) LOCATION: 196..201

-continued

```
        ( D ) OTHER INFORMATION: /function="restriction site"
                / bound_moiety= "Sna BI"

( i x ) FEATURE:
            ( A ) NAME/KEY: protein_bind
            ( B ) LOCATION: 540..545
            ( D ) OTHER INFORMATION: /function="restriction site"
                / bound_moiety= "XbaI"

( x i ) SEQUENCE DESCRIPTION: SEQ ID NO:6:
```

| TGAAAGGAGG | TCACCAAT | ATG | TCA | AAG | TTC | GAT | GAT | TTC | GAT | CTA | GAT | GTT | 51 |
|---|---|---|---|---|---|---|---|---|---|---|---|---|---|
| | | Met | Ser | Lys | Phe | Asp | Asp | Phe | Asp | Leu | Asp | Val | |
| | | -24 | | | | -20 | | | | | -15 | | |

| GTG | AAA | GTC | TCT | AAA | CAA | GAT | TCG | AAA | ATC | ACT | CCG | CAA | TGG | AAA | AGT | 99 |
|---|---|---|---|---|---|---|---|---|---|---|---|---|---|---|---|---|
| Val | Lys | Val | Ser | Lys | Gln | Asp | Ser | Lys | Ile | Thr | Pro | Gln | Trp | Lys | Ser | |
| | | | -10 | | | | | -5 | | | | | 1 | | | |

| ATT | TCA | CTT | TGT | ACA | CCC | GGG | TGT | GTA | ACT | GGT | GCA | TTG | CAA | ACT | TGC | 147 |
|---|---|---|---|---|---|---|---|---|---|---|---|---|---|---|---|---|
| Ile | Ser | Leu | Cys | Thr | Pro | Gly | Cys | Val | Thr | Gly | Ala | Leu | Gln | Thr | Cys | |
| | 5 | | | | | 10 | | | | | 15 | | | | | |

| TTC | CTT | CAA | ACA | CTA | ACT | TGT | AAC | TGC | AAA | ATC | TCT | AAA | TAGGTAACCT | 196 |
|---|---|---|---|---|---|---|---|---|---|---|---|---|---|---|
| Phe | Leu | Gln | Thr | Leu | Thr | Cys | Asn | Cys | Lys | Ile | Ser | Lys | | |
| 20 | | | | | 25 | | | | | 30 | | | | |

| ACGTAGCATC | ACCTTGCTCT | GACTCCTTGC | ACTTCTGAGT | GTTATACATA | CTTATTTTCA | 256 |
|---|---|---|---|---|---|---|
| TAGAGTCGGG | ACAAGAAAAT | GAAGTAAAAA | ACGACGGGTG | TGAAAGAGTT | TATATTCACA | 316 |
| CCCGTTTTTA | TATTCGGCTT | TAAGGAGGAA | CACAATTGTA | GAACGGAAGA | ACGGTTATTT | 376 |
| TCGATCATGC | GTTTTGAATA | ACATTCCAAT | AAAAATTCCA | GTCTCTTCCT | CAAATGCAGA | 436 |
| CAAAGGATGA | AGGACTTAAG | GGTACTTACC | AGGTTTTATG | GTTAAGAATA | TTTCTAAGAA | 496 |
| CATCATATTT | TTTATTAGGA | AATTAATAAA | TGAGATTGAT | CACTCTAGA | | 545 |

```
( 2 ) INFORMATION FOR SEQ ID NO:7:

( i ) SEQUENCE CHARACTERISTICS:
                ( A ) LENGTH: 56 amino acids
                ( B ) TYPE: amino acid
                ( D ) TOPOLOGY: linear ( i i ) MOLECULE TYPE: protein ( x i ) SEQUENCE DESCRIPTION: SEQ ID NO:7:
```

| Met | Ser | Lys | Phe | Asp | Asp | Phe | Asp | Leu | Asp | Val | Val | Lys | Val | Ser | Lys |
|---|---|---|---|---|---|---|---|---|---|---|---|---|---|---|---|
| -24 | | | | -20 | | | | -15 | | | | | -10 | | |

| Gln | Asp | Ser | Lys | Ile | Thr | Pro | Gln | Trp | Lys | Ser | Ile | Ser | Leu | Cys | Thr |
|---|---|---|---|---|---|---|---|---|---|---|---|---|---|---|---|
| | | | -5 | | | | | 1 | | | | 5 | | | |

| Pro | Gly | Cys | Val | Thr | Gly | Ala | Leu | Gln | Thr | Cys | Phe | Leu | Gln | Thr | Leu |
|---|---|---|---|---|---|---|---|---|---|---|---|---|---|---|---|
| | 10 | | | | | 15 | | | | | 20 | | | | |

| Thr | Cys | Asn | Cys | Lys | Ile | Ser | Lys |
|---|---|---|---|---|---|---|---|
| 25 | | | | | 30 | | |

```
( 2 ) INFORMATION FOR SEQ ID NO:8:

( i ) SEQUENCE CHARACTERISTICS:
                ( A ) LENGTH: 545 base pairs
                ( B ) TYPE: nucleic acid
                ( C ) STRANDEDNESS: unknown
                ( D ) TOPOLOGY: unknown ( i i ) MOLECULE TYPE: DNA (genomic)

( i x ) FEATURE:
                ( A ) NAME/KEY: CDS
                ( B ) LOCATION: 19..186

( i x ) FEATURE:
                ( A ) NAME/KEY: mat_peptide
```

(B) LOCATION: 91..186

(ix) FEATURE:
    (A) NAME/KEY: protein_bind
    (B) LOCATION: 9..15
    (C) IDENTIFICATION METHOD: experimental
    (D) OTHER INFORMATION: /function="restriction site"
        / bound_moiety= "BstEII"
        / evidence= EXPERIMENTAL (ix) FEATURE:
    (A) NAME/KEY: protein_bind
    (B) LOCATION: 42..47
    (D) OTHER INFORMATION: /function="restriction site"
        / bound_moiety= "Xba I"

(ix) FEATURE:
    (A) NAME/KEY: protein_bind
    (B) LOCATION: 72..78
    (D) OTHER INFORMATION: /function="restriction site"
        / bound_moiety= "Bst BI"

(ix) FEATURE:
    (A) NAME/KEY: protein_bind
    (B) LOCATION: 115..120

(ix) FEATURE:
    (A) NAME/KEY: protein_bind
    (B) LOCATION: 189..195

(ix) FEATURE:
    (A) NAME/KEY: protein_bind
    (B) LOCATION: 196..201
    (D) OTHER INFORMATION: /function="restriction site"
        / bound_moiety= "Sna BI"

(ix) FEATURE:
    (A) NAME/KEY: protein_bind
    (B) LOCATION: 540..545
    (D) OTHER INFORMATION: /function="restriction site"
        / bound_moiety= "XbaI"

(xi) SEQUENCE DESCRIPTION: SEQ ID NO:8:

```
TGAAAGGAGG  TCACCAAT  ATG  TCA  AAG  TTC  GAT  GAT  TTC  GAT  CTA  GAT  GTT              51
                     Met  Ser  Lys  Phe  Asp  Asp  Phe  Asp  Leu  Asp  Val
                     -24            -20                      -15

GTG  AAA  GTC  TCT  AAA  CAA  GAT  TCG  AAA  ATC  ACT  CCG  CAA  TGG  AAA  AGT           99
Val  Lys  Val  Ser  Lys  Gln  Asp  Ser  Lys  Ile  Thr  Pro  Gln  Trp  Lys  Ser
               -10                      -5                           1

ATT  GCA  CTT  TGT  ACA  CCC  GGG  TGT  GTA  ACT  GGT  GCA  TTG  CAA  ACT  TGC          147
Ile  Ala  Leu  Cys  Thr  Pro  Gly  Cys  Val  Thr  Gly  Ala  Leu  Gln  Thr  Cys
          5                        10                       15

TTC  CTT  CAA  ACA  CTA  ACT  TGT  AAC  TGC  AAA  ATC  TCT  AAA  TAGGTAACCT             196
Phe  Leu  Gln  Thr  Leu  Thr  Cys  Asn  Cys  Lys  Ile  Ser  Lys
 20                       25                       30

ACGTAGCATC  ACCTTGCTCT  GACTCCTTGC  ACTTCTGAGT  GTTATACATA  CTTATTTTCA                  256

TAGAGTCGGG  ACAAGAAAAT  GAAGTAAAAA  ACGACGGGTG  TGAAAGAGTT  TATATTCACA                  316

CCCGTTTTTA  TATTCGGCTT  TAAGGAGGAA  CACAATTGTA  GAACGGAAGA  ACGGTTATTT                  376

TCGATCATGC  GTTTTGAATA  ACATTCCAAT  AAAAATTCCA  GTCTCTTCCT  CAAATGCAGA                  436

CAAAGGATGA  AGGACTTAAG  GGTACTTACC  AGGTTTTATG  GTTAAGAATA  TTTCTAAGAA                  496

CATCATATTT  TTTATTAGGA  AATTAATAAA  TGAGATTGAT  CACTCTAGA                               545
```

(2) INFORMATION FOR SEQ ID NO:9:

(i) SEQUENCE CHARACTERISTICS:
        (A) LENGTH: 56 amino acids
        (B) TYPE: amino acid
        (D) TOPOLOGY: linear (i i) MOLECULE TYPE: protein (x i) SEQUENCE DESCRIPTION: SEQ ID NO:9:

| Met | Ser | Lys | Phe | Asp | Asp | Phe | Asp | Leu | Asp | Val | Val | Lys | Val | Ser | Lys |
|-----|-----|-----|-----|-----|-----|-----|-----|-----|-----|-----|-----|-----|-----|-----|-----|
| -24 |     |     |     | -20 |     |     |     | -15 |     |     |     | -10 |     |     |     |

| Gln | Asp | Ser | Lys | Ile | Thr | Pro | Gln | Trp | Lys | Ser | Ile | Ala | Leu | Cys | Thr |
|-----|-----|-----|-----|-----|-----|-----|-----|-----|-----|-----|-----|-----|-----|-----|-----|
|     |     |     | -5  |     |     |     |     | 1   |     |     |     | 5   |     |     |     |

| Pro | Gly | Cys | Val | Thr | Gly | Ala | Leu | Gln | Thr | Cys | Phe | Leu | Gln | Thr | Leu |
|-----|-----|-----|-----|-----|-----|-----|-----|-----|-----|-----|-----|-----|-----|-----|-----|
|     | 10  |     |     |     | 15  |     |     |     |     |     |     | 20  |     |     |     |

| Thr | Cys | Asn | Cys | Lys | Ile | Ser | Lys |
|-----|-----|-----|-----|-----|-----|-----|-----|
| 25  |     |     |     |     | 30  |     |     |

(2) INFORMATION FOR SEQ ID NO:10:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:10:

GGCGTTACCT TTTCATAACG TGTGAAACAT GTGGGCCCAA CTTCGAAACC A     51

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: unknown
        (D) TOPOLOGY: linear (i i) MOLECULE TYPE: DNA (genomic)

(x i) SEQUENCE DESCRIPTION: SEQ ID NO:11:

TGAATTCAGA TTCGAAAATC ACTCCGCAAT GGAAAAGT     38

(2) INFORMATION FOR SEQ ID NO:12:

(i) SEQUENCE CHARACTERISTICS:
        (A) LENGTH: 42 base pairs
        (B) TYPE: nucleic acid
        (C) STRANDEDNESS: unknown
        (D) TOPOLOGY: linear (i i) MOLECULE TYPE: DNA (genomic)

(x i) SEQUENCE DESCRIPTION: SEQ ID NO:12:

AGAATTCACA CCCGGGTGTG TAACTGGTGC ATTGCAAACT TG     42

(2) INFORMATION FOR SEQ ID NO:13:

(i) SEQUENCE CHARACTERISTICS:
        (A) LENGTH: 11 base pairs
        (B) TYPE: nucleic acid
        (C) STRANDEDNESS: unknown
        (D) TOPOLOGY: linear (i i) MOLECULE TYPE: DNA (genomic)

(x i) SEQUENCE DESCRIPTION: SEQ ID NO:13:

CATGTGGTCC T     11

(2) INFORMATION FOR SEQ ID NO:14:

(i) SEQUENCE CHARACTERISTICS:

(A) LENGTH: 37 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO:14:

ACACATTGAC CACGTAACGT TTGAACGAAG GAAGTTT 37

(2) INFORMATION FOR SEQ ID NO:15:

(i) SEQUENCE CHARACTERISTICS:
(A) LENGTH: 36 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO:15:

AAACACACTA ACTTGTAACT GCAAAATCTC TAAATA 36

(2) INFORMATION FOR SEQ ID NO:16:

(i) SEQUENCE CHARACTERISTICS:
(A) LENGTH: 10 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO:16:

AGTAAAACCA 10

(2) INFORMATION FOR SEQ ID NO:17:

(i) SEQUENCE CHARACTERISTICS:
(A) LENGTH: 45 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO:17:

GAACATTGAC GTTTTAGAGA TTTATCCATT GGGGTTTCGA AAGTG 45

(2) INFORMATION FOR SEQ ID NO:18:

(i) SEQUENCE CHARACTERISTICS:
(A) LENGTH: 47 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO:18:

GGAATCATAG GTAACCTACG TAGCATCACC TTGCTCTGAC TCCTTGC 47

(2) INFORMATION FOR SEQ ID NO:19:

(i) SEQUENCE CHARACTERISTICS:
(A) LENGTH: 12 base pairs
(B) TYPE: nucleic acid
(C) STRANDEDNESS: unknown
(D) TOPOLOGY: linear ( i i ) MOLECULE TYPE: DNA (genomic)

( x i ) SEQUENCE DESCRIPTION: SEQ ID NO:19:

CATTTTGGTA AT      12

( 2 ) INFORMATION FOR SEQ ID NO:20:

( i ) SEQUENCE CHARACTERISTICS:
        ( A ) LENGTH: 31 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:20:

CGTAGTGGAA CGAGACTGAG GAACGTGAAG A      31

( 2 ) INFORMATION FOR SEQ ID NO:21:

( i ) SEQUENCE CHARACTERISTICS:
        ( A ) LENGTH: 39 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:21:

ATATTTTTA TTAGGAAATT AATAAATGAG ATTGATCAC      39

( 2 ) INFORMATION FOR SEQ ID NO:22:

( i ) SEQUENCE CHARACTERISTICS:
        ( A ) LENGTH: 45 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:22:

CCTTTAATTA TTTACTCTAA CTAGTGAGAT CTAACTTCGA AGACG      45

( 2 ) INFORMATION FOR SEQ ID NO:23:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

Trp Lys Ser Ile Ser Leu Cys Thr Pro Gly Cys Val Thr Gly Ala Leu
 1              5                    10                  15

Gln Thr Cys Phe Leu Gln Thr Leu Thr Cys Asn Cys Lys Ile Ser Lys
               20                  25              30

( 2 ) INFORMATION FOR SEQ ID NO:24:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Trp Lys Ser Ile Ala Leu Cys Thr Pro Gly Cys Val Thr Gly Ala Leu
 1               5                  10                      15

Gln Thr Cys Phe Leu Gln Thr Leu Thr Cys Asn Cys Lys Ile Ser Lys
            20              25                      30
```

( 2 ) INFORMATION FOR SEQ ID NO:25:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

```
Met Ser Thr Lys Asp Phe Asn Leu Asp Leu Val Ser Val Ser Lys Lys
 1               5                  10                      15

Asp Ser Gly Ala Ser Pro Arg
            20
```

( 2 ) INFORMATION FOR SEQ ID NO:26:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

```
Met Ser Lys Phe Asp Asp Phe Asp Leu Asp Val Val Lys Val Ser Lys
 1               5                  10                      15

Gln Asp Ser Lys Ile Thr Pro Gln
            20
```